(12) United States Patent
Aboagye et al.

(10) Patent No.: US 8,236,985 B2
(45) Date of Patent: Aug. 7, 2012

(54) COMPOUNDS AND USES THEREOF

(75) Inventors: Eric Ofori Aboagye, London (GB);
David Michael Vigushin, London (GB);
Wendy Vigushin, legal representative, London (GB)

(73) Assignee: Imperial Innovations Ltd., London (GB)

( * ) Notice: Subject to any disclaimer, the term of this patent is extended or adjusted under 35 U.S.C. 154(b) by 558 days.

(21) Appl. No.: 12/447,006

(22) PCT Filed: Oct. 24, 2007

(86) PCT No.: PCT/GB2007/004069
§ 371 (c)(1),
(2), (4) Date: Nov. 16, 2009

(87) PCT Pub. No.: WO2008/050125
PCT Pub. Date: May 2, 2008

(65) Prior Publication Data
US 2010/0063144 A1 Mar. 11, 2010

(30) Foreign Application Priority Data
Oct. 24, 2006 (GB) .................................. 0621160.1

(51) Int. Cl.
*C07C 259/06* (2006.01)
*A61K 31/19* (2006.01)

(52) U.S. Cl. ........................................ 562/621; 514/575

(58) Field of Classification Search .................. 562/621; 514/575
See application file for complete search history.

(56) References Cited

U.S. PATENT DOCUMENTS
2002/0086890 A1 * 7/2002 Levin et al. .................... 514/357

OTHER PUBLICATIONS

Benn et al., "Cytotoxic Compounds, Part II. Some Amides of the 'Nitrogen Mustard' Type," Journal of the Chemical Society pp. 2365-2375 (1961).
Hill et al., "Selectivity of Action of Alkylating Agents and Drug Resistance. 4. Synthesis of Tritium-labeled Chlorambucil and a Study o fits Cellular Uptake by Drug-sensitive and Drug-resistant Strains of the Yoshida Ascites Sarcoma In Vitro," Journal opf Medicinal Chemistry 14(7):614-8 (1971).
International Search Report for International Patent Application No. PCT/GB2007/004069 (Apr. 3, 2008).
Roehrig et al., "Synthesis and Antitumor Activity of 4-[p-[bis(2-chloroethyl)amino]phenyl]butyrates," Journal of Pharmaceutical Sciences 69(10):1232-4 (1980).
Schatzschneider et al., "Bifunctional Rhodium Intercalator Conjugates as Mismatch-directing DNA Alkylating Agents," Journal of the American Chemical Society 126(28):8630-1 (2004).
Schatzschneider et al., "Bifunctional Rhodium Intercalator Conjugates as Mismatch-directing DNA Alkylating Agents," Supporting Information, Compound 11. Journal of the American Chemical Society 126(28):S1-S10 (2004).
Tercel et al., "Hypoxia-selective Antitumor Agents. 11. Chlorambucil N-oxide: A Reappraisal of its Synthesis, Stability, and Selective Toxicity for Hypoxic Cells," Journal of Medicinal Chemistry 38(7):1247-52 (1995).
Valu et al., "DNA-directed Alkylating Agents. 3. Structure-activity Relationships for Acridine-linked Aniline Mustards: Consequences of Varying the Length of the Linker Chain," Journal of Medicinal Chemistry 33(11):3014-9 (1990).
Written Opinion of the International Searching Authority for International Patent Application No. PCT/GB2007/004069 (Apr. 3, 2008).
Yoshida et al., "Potent and Specific Inhibition of Mammalian Histone Deacetylase Both In Vivo and In Vitro by Trichostatin A," Journal of Biological Chemistry 265(28):17174-9 (1990).
Benn et al., "Cytotoxic Compounds. Part V. Derivatives of p-(NN-Di-2-chloroethyl- and of p-(NN-Di-2-bromoethyl-amino)benzenesulphonic Acid," J. Chem. Soc. pp. 3395-3400 (1964).
Dignam et al., "Accurate Transcription Initiation by RNA Polymerase II in a Soluble Extract From Isolated Mammalian Nuclei," Nucleic Acids Res. 11(5):1475-1489 (1983).
Elderfield et al., "Synthesis of Potential Anticancer Agents. I. Nitrogen Mustards Derived From p-[N,N-Bis(2-chloroethyl)amino]benzaldehyde," J. Org. Chem. 23:1749-1753 (1958).
Emiliani et al., "Characterization of a Human RPD3 Ortholog, HDAC3," Proc. Natl. Acad. Sci. USA 95:2795-2800 (1998).
Finnin et al., "Structures of a Histone Deacetylase Homologue Bound to the TSA and SAHA Inhibitors," Nature 401:188-193 (1999).
Furumai et al., "Potent Histone Deacetylase Inhibitors Built From Trichostatin A and Cyclic Tetrapeptide Antibiotics Including Trapoxin," Proc. Natl. Acad. Sci. USA 98(1):87-92 (2001).
Leyton et al., "In vivo Biological Activity of the Histone Deacetylase Inhibitor LAQ824 Is Detectable With 3'-Deoxy-3'-[18F]Fluorothymidine Positron Emission Tomography," Cancer Res. 66(15):7621-7629 (2006).

(Continued)

*Primary Examiner* — Shailendra Kumar
(74) *Attorney, Agent, or Firm* — LeClairRyan, a Professional Corporation

(57) ABSTRACT

There is provided a compound of formula (I) wherein $R^{1a}$, $R^{2a}$, $R^3$, $X^1$ to $X^6$, a, b and c have meanings given in the description, which compounds are useful as, or are useful as prodrugs of, inhibitors of HDAC enzyme activity, and thus, in particular, in the treatment of conditions where inhibition of HDAC enzyme activity is required.

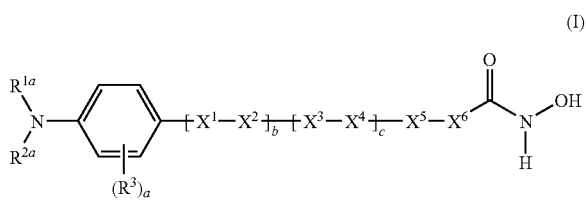

(I)

21 Claims, 19 Drawing Sheets

OTHER PUBLICATIONS

Figure 1:
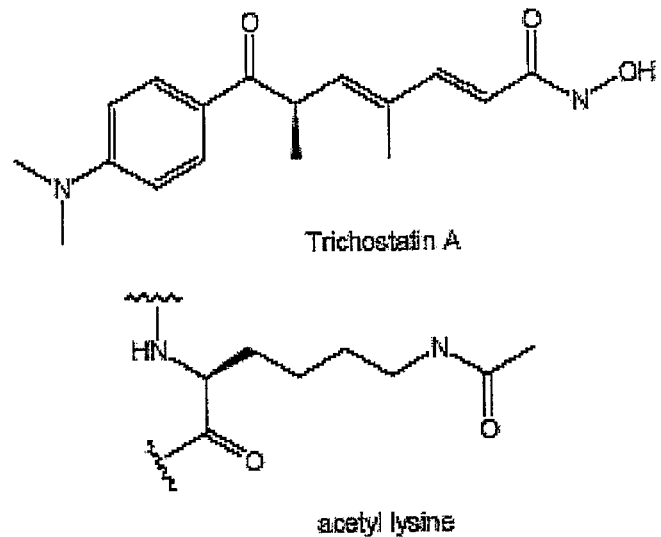

Marks et al., "Histone Deacetylase Inhibitors: Inducers of Differentiation or Apoptosis of Transformed Cells," J. Natl. Cancer Inst. 92(15):1210-1216 (2000).

Marson et al., "Stereodefined and Polyunsaturated Inhibitors of Histone Deacetylase Based on (2E,4E)-5-arylpenta-2,4-dienoic Acid Hydroxyamides," Bioorg. Med. Chem. Lett. 14:2477-2481 (2004).

Sanderson et al., "Plasma Pharmacokinetics and Metabolism of the Histone Deacetylase Inhibitor Trichostatin A After Intraperitoneal Administration to Mice," Drug Metab. Dispos. 32(10):1132-1138 (2004).

Skehan et al., "New Colorimetric Cytotoxicity Assay for Anticancer-Drug Screening," J. Natl. Cancer Inst. 82:1107-1112 (1990).

Stella et al., "Prodrugs: A Chemical Approach to Targeted Drug Delivery," in Borchardt eds., Directed Drug Delivery, Humana Press, pp. 247-267 (1985).

Taunton et al., "A Mammalian Histone Deacetylase Related to the Yeast Transcriptional Regulator Rpd3p," Science 272:408-411 (1996).

Toja et al., "New Classes of Antimuscarinic Agents Endowed With Selective Antispasmodic Properties," Arzneim.-Forsch/Drug Res. 44(1):501-509 (1994).

Tsuji et al., "A New Antifungal Antibiotic, Trichostatin," J. Antibiot. 29(1):1-6 (1976).

Tsuji and Kobayashi, "Trichostatin C, A Glucopyranosyl Hydroxamate," J. Antibiot. 31(10):939-944 (1978).

Vigushin et al., "Trichostatin A Is a Histone Deacetylase Inhibitor With Potent Antitumor Activity Against Breast Cancer in Vivo," Clin. Cancer Res. 7:971-976 (2001).

Vigushin and Coombes, "Targeted Histone Deacetylase Inhibition for Cancer Therapy," Curr. Cancer Drug Targets 4(2):205-218 (2004).

Wilman, "Prodrugs in Cancer Chemotherapy," Biochemical Society Transactions 14:375-382 (1986).

Yoshida et al., "Effects of Trichostatins on Differentiation of Murine Erythroleukemia Cells," Cancer Res. 47:3688-3691 (1987).

Yoshida et al., "Structural Specificity for Biological Activity of Trichostatin A, A Specific Inhibitor of Mammalian Cell Cycle With Potent Differentiation-Inducing Activity in Friend Leukemia Cells," J. Antibiot. 43:1101-1106 (1990).

* cited by examiner

Figure 3: page 1
(A)
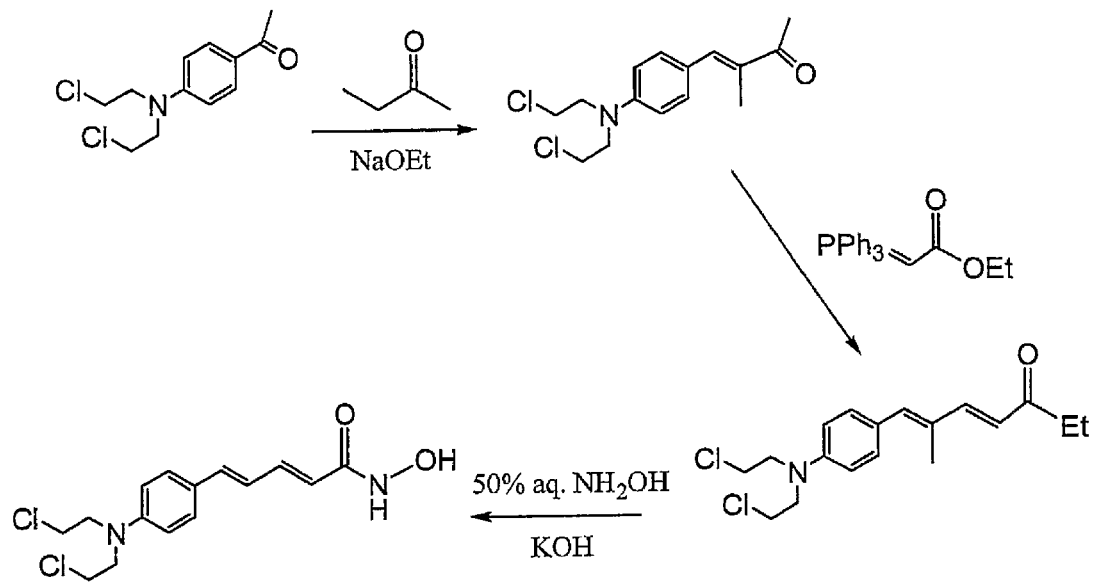
(B)
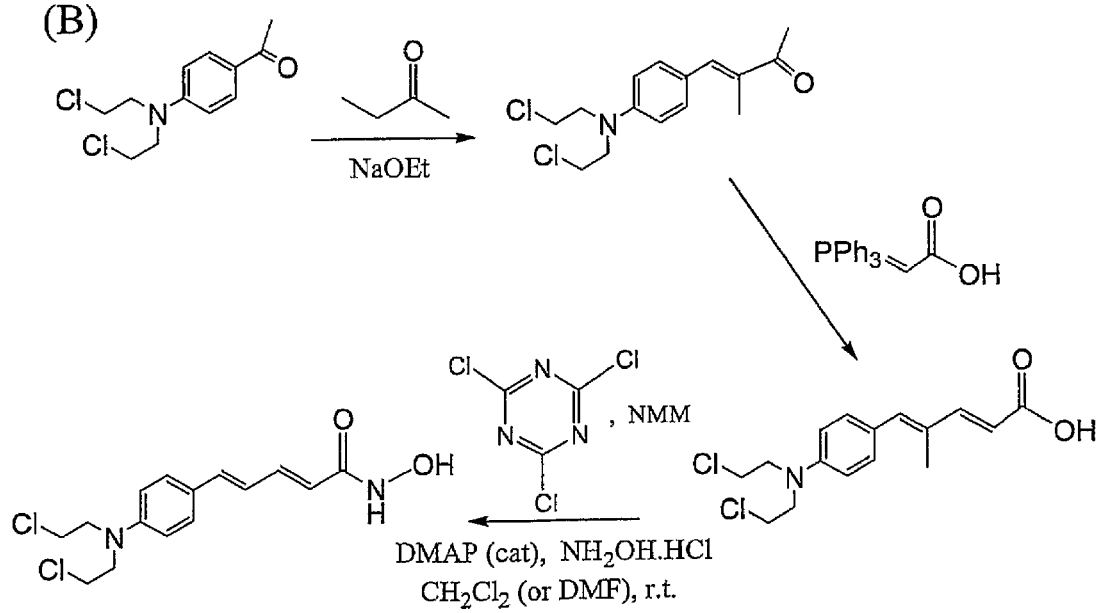

Figure 3: page 2
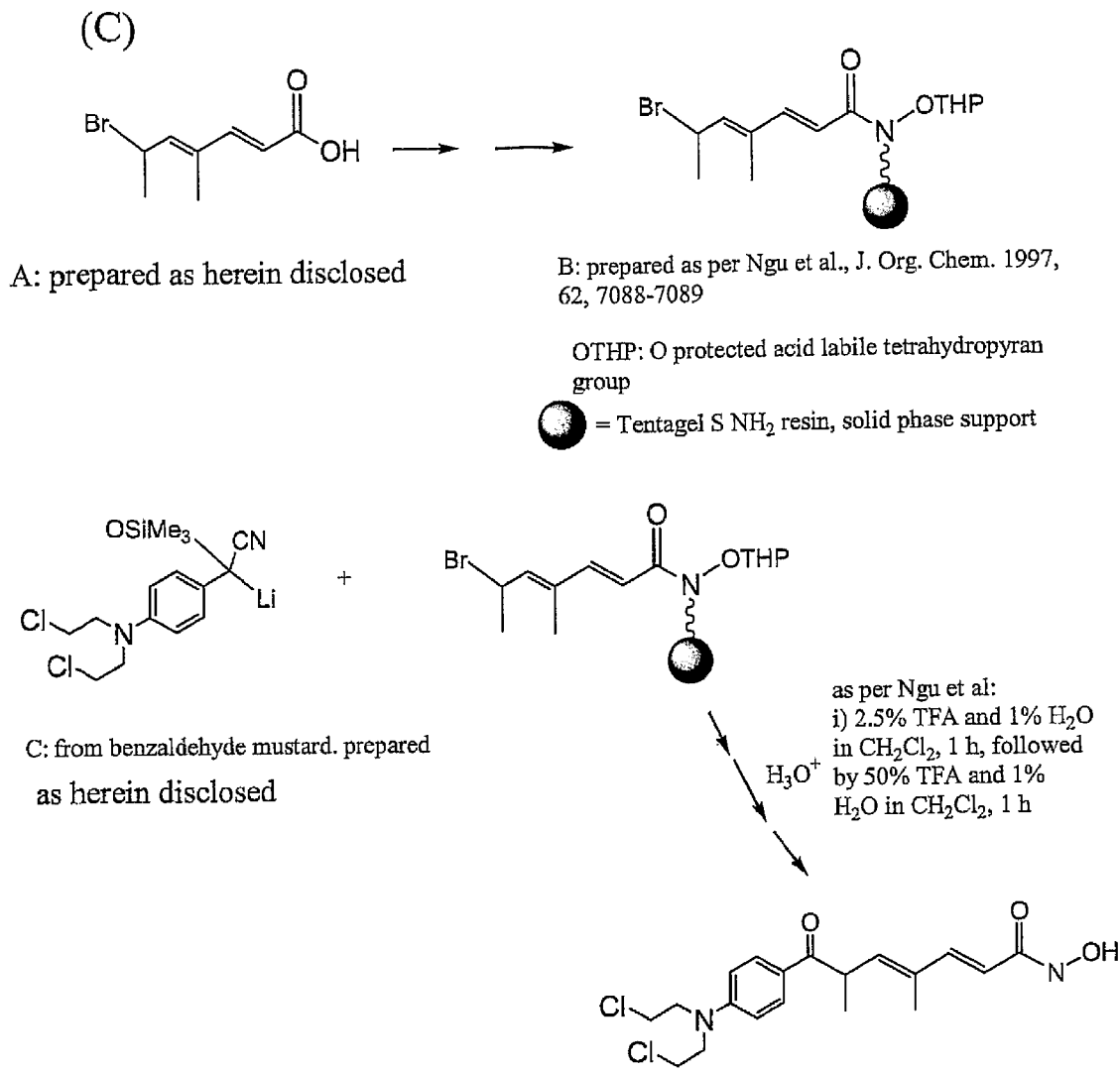

Figure 9
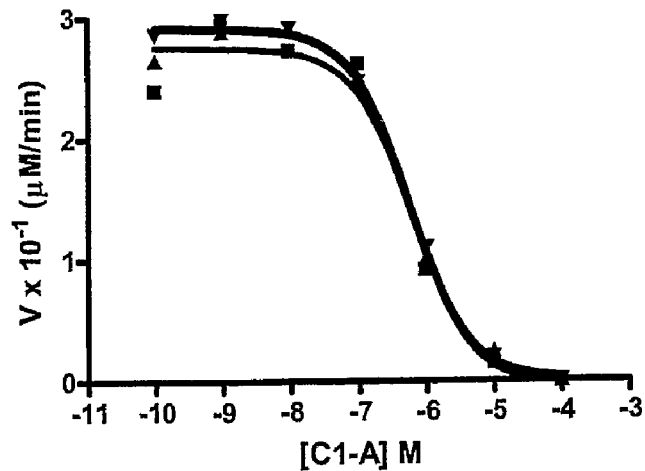
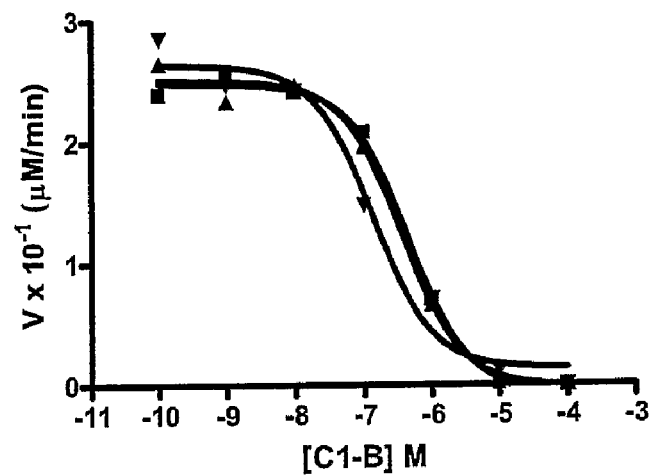
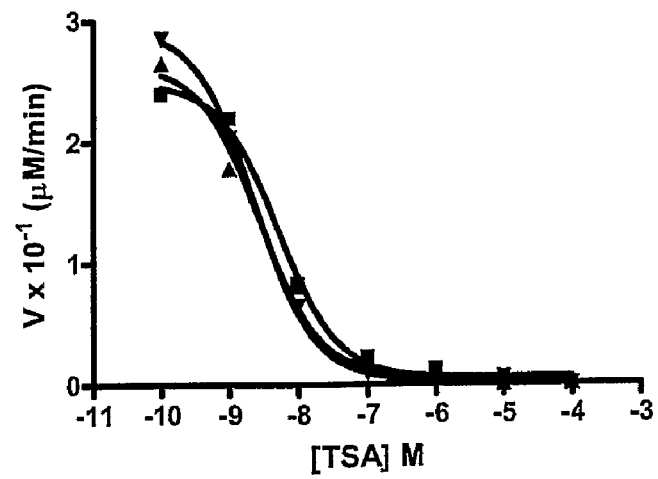

Figure 10
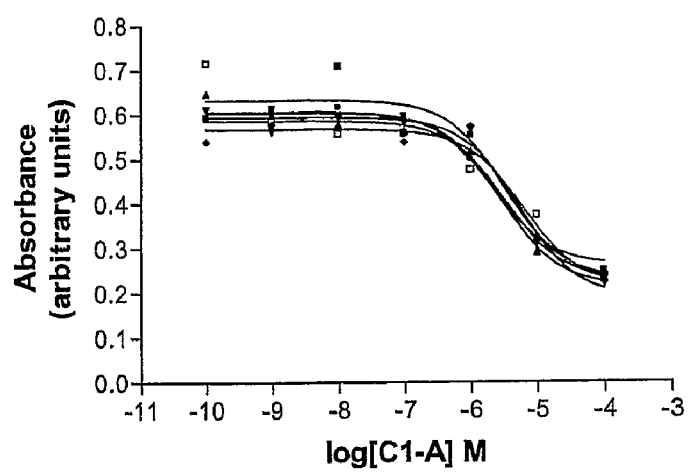
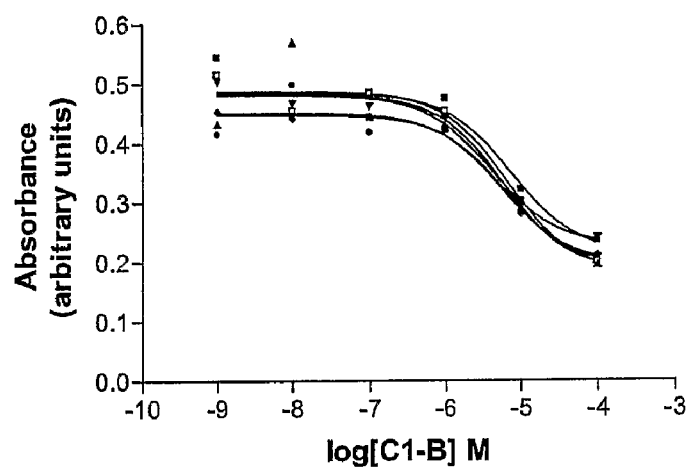
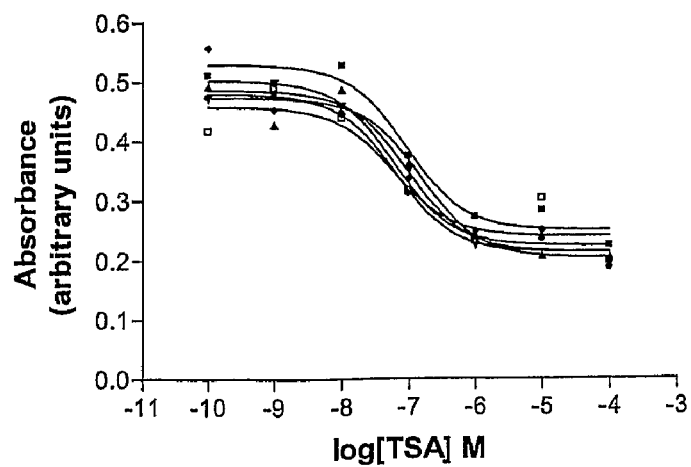

Vehicle= 10%DMSO, 5% Tween 20 & 85% Saline

COMPOUNDS AND USES THEREOF

This application is a national stage application under 35 U.S.C. §371 from PCT Application No. PCT/GB2007/004069, filed Oct. 24, 2007, which claims the priority benefit of Great Britain Application No. 0621160.1, filed Oct. 24, 2006.

The present invention relates to histone deacetylase inhibitors, particularly mustard prodrug hydroxamic acid-based histone deacetylase inhibitors (MPHis) and uses of said inhibitors as, for example, anticancer agents.

Histone deacetylase inhibitors (HDACis) are emerging as a promising new class of anticancer drugs that selectively inhibit tumour cell proliferation. The mechanisms of inhibition of cell proliferation are thought to include regulation of gene transcription, $G_1$/S cell cycle arrest through induction of p21 and downregulation of cyclin D1, $G_2$/M arrest by inhibition of α-tubulin, and induction of differentiation or apoptosis (tumour-type dependent).

HDACis induce reversible posttranslational hyperacetylation of ε-amino groups of highly conserved lysine residues in nucleosome core histones that are important in the modification of chromatin super-structure and accessibility of the transcriptional apparatus to promoters of target genes. Global acetylation status is determined by the opposing activities of histone acetyl transferase (HAT) and HDAC enzymes. Histone hyperacetylation is in general associated with transcriptional activation of certain genes, e.g. CDKN1A (the gene for p21), but also repression of others, e.g., CCND1 which encodes cyclin D1. In addition to histones, other cellular proteins are also modified by acetylation including transcription factors, e.g., p53, oestrogen receptor, E2F and α-tubulin. Acetylation, therefore, plays a role in multiple diverse cellular processes (reviewed in Vigushin and Coombes (2004) *Curr. Cancer Drug Targets* 4, 205-218).

Trichostatin A (TSA) and its glucopyranosyl derivative trichostatin C are hydroxamic acids that were first isolated from cultures of *Streptomyces hygroscopicus* as antifungal antibiotics active against *Trichophyton* sp. (Tsuji et al., *J. Antibiot.* (Tokyo) (1976) 29: 1-6; Tsuji and Kobayashi, *J. Antibiot.* (Tokyo) (1978) 31: 939-944). TSA was subsequently found to exhibit potent cytostatic and differentiating activity at nanomolar concentrations against Friend murine erythroleukaemia cells in culture (Yoshida et al, (1987), *Cancer Res.*, 47: 3688-91.). Later work identified similar antiproliferative activity against a broad range of human tumour-derived cell lines (reviewed in Vigushin and Coombes, loc. cit.). Stereoselective synthesis of the enantiomers of TSA and subsequent analysis showed that the natural configuration is R-(+)-TSA and S-(−)-TSA is 70 times less biologically active (Yoshida et al., (1990) *J. Antibiot.* (Tokyo) 43: 1101-1106). Nuclear histones from cells treated with TSA were found to be highly acetylated and on pulse-chase analysis this was due to decreased deacetylation rather than increased acetylation (Yoshida et al., (1990) *J. Biol. Chem.* 265: 17174-17179). This observation led to the subsequent identification of histone deacetylase (HDAC) as the specific molecular target of TSA (Yoshida et al., ibid.).

TSA is a potent, specific and reversible inhibitor of HDAC at low nanomolar concentrations. The hydroxamic acid moiety and the natural R-(+)-configuration of the chiral centre at the 6-position are essential for this activity. TSA acts as a substrate mimic; the aliphatic chain and hydroxamic acid are analogous to the lysine side chain and acetyl group of the histone substrate, respectively (FIG. 1). The X-ray crystal structure of the HDAC catalytic core is known to atomic resolution from crystallisation of the histone-deacetylase-like protein (HDLP). Co-crystallisation of HDLP with TSA have indicated the following (Finnin et al. (1999) *Nature* 401, 188-193): (a) The catalytic core has an a α/β motif and the active site comprises a tubular pocket with $Zn^{2+}$ binding site and two asparagine-histidine charge-relay systems. (b) TSA binds inside the pocket by inserting the aliphatic chain into the tube, making contact with residues at the rim, walls, and at the bottom where the hydroxamic acid coordinates a $Zn^{2+}$ in a bidentate fashion; chelation of $Zn^{2+}$ by the hydroxamic acid moiety is the main mechanism of HDAC enzyme inhibition; this property is specific to the HDAC enzyme rather than circulating $Zn^{2+}$ or other $Zn^{2+}$-containing enzymes. (c) The N-dimethyl-aminophenyl group (FIG. 1) acts as a cap to pack the inhibitor at the rim of the tubular active site pocket.

Histone deacetylase (HDAC) inhibitors have been shown to be potent inducers of growth arrest, differentiation, and/or apoptotic cell death of transformed cells in vitro and in vivo (Marks et al., *J. Natl. Cancer Inst.* 92 (15): 1210). The compounds trapoxin B and depudecin irreversibly bind to HDAC and inhibit its activity at nano-molar and micromolar concentrations, respectively.

We have recently observed that TSA administered subcutaneously at 500 μg/kg/day for 4 weeks had potent anti-tumour activity without significant toxicity in vivo in the N-methyl-N-nitrosourea carcinogen-induced rat mammary cancer model (Vigushin et al. (2001) *Clin. Cancer Res.* 7, 971-976).

Figure 2:
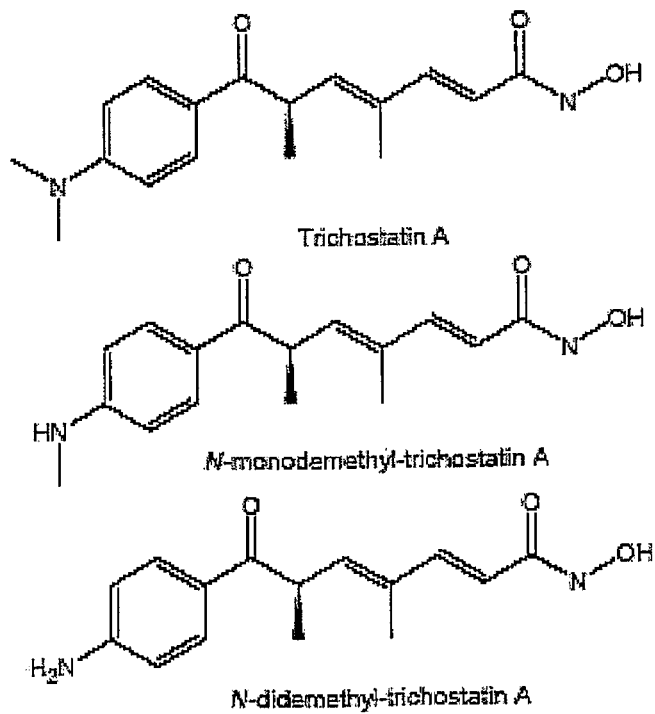

Our subsequent studies in immunodeficient mice bearing MCF7 and MDA-MB-435 human mammary tumour xenografts showed anti-tumour activity following intra-peritoneal injection at 20-40 mg/kg/day for 2 weeks. Plasma pharmacokinetic studies of TSA administered intraperitoneally to mice at 80 mg/kg showed rapid and extensive metabolism of the parent compound. The half-life of TSA was 6.3 min and $C_{max}$ 40 μg/ml. Parent compound and phase I metabolites were separated by HPLC and detected with simultaneous UV and positive ion electrospray mass spectrometry. Metabolites were identified by positive ion electrospray tandem mass spectrometry. N-demethylated TSA was a major metabolite (FIG. 2). The primary phase I biotransformation pathways were N-demethylation, reduction of the hydroxamic acid to the corresponding TSA amide, and oxidative deamination to trichostatic acid (Sanderson et al., *Drug Metab. Dispos.* (2004) 32(10):1132-8).

Our studies have also shown that, of the HPLC fractions tested for HDAC inhibitory activity in vitro, only the fractions corresponding to the parent compound and N-monodemethylated TSA were active; the N-demethylated TSA metabolite and TSA were equipotent. This suggests that changes to the N-dimethyl-aminophenyl group of TSA are tolerated, i.e. it may be possible to modify this region of TSA without adversely affecting HDAC inhibitory activity (Sanderson et al., ibid.).

While TSA is active in vivo in models of breast cancer the compound has poor pharmacokinetics. Therefore, there remains a need for TSA derivatives that provide potent HDAC inhibition and enhanced cytostasis while having a good therapeutic index and reduced frequency of administration.

The compounds of the present invention provide such derivatives. Modifying the N-dimethyl-aminophenyl group of TSA to include a nitrogen mustard moiety will allow the derived TSA-compound to maintain the biological activity of TSA but, in addition, have reduced metabolism and enhanced binding to HDAC. The TSA-derivatives are mustard pro-drug hydroxamic acid-based HDAC inhibitors (MPHis).

The nitrogen mustard moiety will act synergistically with the hydroxamic acid moiety to enhance binding of the MPHis compound to the target, for example HDAC.

According to a first aspect of the invention there is provided a compound of formula I:

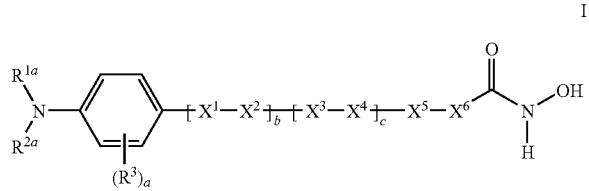

wherein
$R^{1a}$ represents $C_{1-4}$ alkyl (which latter group is optionally substituted by one or more substituents selected from halogeno and aryl), aryl, $(CH_2)_2$-$L^1$ or the structural fragment

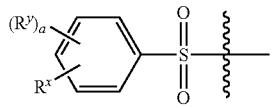

wherein $R^x$ represents H or $N(R^{1b})R^{2b}$;
$R^{1b}$ and $R^{2b}$ independently represent $C_{1-4}$ alkyl (which latter group is optionally substituted by one or more substituents selected from halogeno and aryl), aryl or $(CH_2)_2$-$L^2$;
$R^y$ represents halogeno or $C_{1-4}$ alkyl;
$R^{2a}$ represents H, $C_{1-4}$ alkyl (which latter group is optionally substituted by one or more substituents selected from halogen and aryl), aryl or $(CH_2)_2$-$L^3$;
$L^1$, $L^2$ and $L^3$ each represents, independently at each occurrence, a leaving group;
$R^3$ represents halogeno or $C_{1-4}$ alkyl;
a represents, independently at each occurrence, an integer from 0 to 4;
$X^1$—$X^2$ represents $C(O)$—$CH(Y^1)$, $C(H)$=$C(Y^1)$, $CH_2$—$CH(Y^1)$, $NH$—$CH(Y^1)$, $CH_2$—$C(O)$, $NH$—$C(O)$ or $CH(Y^1)$;
b represents 0 or 1;
$X^3$—$X^4$ represents $CH$=$C(Y^2)$, $O$—$CH(Y^2)$, $NH$—$CH(Y^2)$, $O$—$C(O)$ or $NH$—$C(O)$;
c represents an integer from 0 to 10;
$X^5$—$X^6$ represents $CH_2$—$CH_2$, $CH$=$CH$ or $O$—$CH_2$; and
$Y^1$ and $Y^2$ independently represent, at each occurrence, H or $C_{1-4}$ alkyl;
or a pharmaceutically acceptable derivative thereof,
provided that at least one of the following is the case:
(a) $R^{1a}$ represents $(CH_2)_2$-$L^1$;
(b) $R^{1b}$ and/or $R^{2b}$ represents $(CH_2)_2$-$L^2$;
(c) $R^2$ represents $(CH_2)_2$-$L^3$.

The term "leaving group", when used herein, includes references to halogeno (e.g. Cl, Br, I) and $OS(O)_2R^4$ groups wherein $R^4$ is $C_{1-8}$ alkyl (optionally substituted by one or more fluoro atoms) or aryl (optionally substituted by one or more substituents selected from $C_{1-4}$ alkyl, $C_{1-4}$ alkoxy, $NO_2$ and halogeno).

While not being bound to any particular theory, we consider that the compounds of the first aspect of the invention will bind to a $Zn^{2+}$ within the active site pocket of HDAC enabling a mesomeric or positive inductive transfer of electron to the nitrogen mustard group. Hence there is an synergistic interaction between the reaction of the hydroxyamic acid moiety with the $Zn^{2+}$ of the HDAC enzyme and the nitrogen mustard group that results in a formation of an aziridine which can alkylate the HDAC enzyme and lead to irreversible inactivation of HDAC. Therefore the compounds are considered to have similar in vitro HDAC potency but greatly prolonged duration of action in biological systems. Hence the compounds are considered to have a good therapeutic index and require a reduced frequency of administration to the patient.

Unless otherwise specified, alkyl groups and alkoxy groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halogen, and especially fluoro, atoms.

When used herein, the term "aryl" includes references to $C_{6-10}$ aryl groups such as phenyl, naphthyl and the like. Unless otherwise specified, aryl groups are optionally substituted by one or more substituents selected from halogeno, $C_{1-4}$ alkyl and $C_{1-4}$ alkoxy. When substituted, aryl groups are preferably substituted by one to five (e.g. one to three) substituents.

Pharmaceutically acceptable derivatives include salts and solvates. Salts which may be mentioned include acid addition salts.

According to a further aspect of the invention there is provided a compound of formula I:

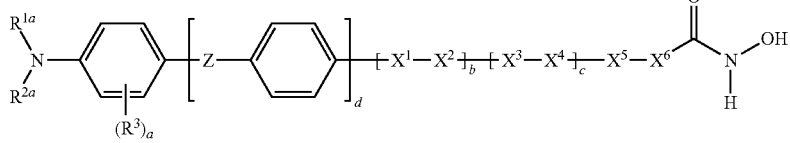

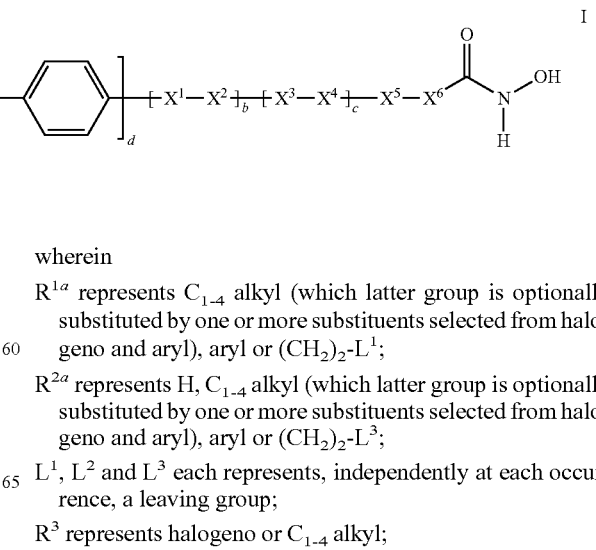

wherein
$R^{1a}$ represents $C_{1-4}$ alkyl (which latter group is optionally substituted by one or more substituents selected from halogeno and aryl), aryl or $(CH_2)_2$-$L^1$;
$R^{2a}$ represents H, $C_{1-4}$ alkyl (which latter group is optionally substituted by one or more substituents selected from halogeno and aryl), aryl or $(CH_2)_2$-$L^3$;
$L^1$, $L^2$ and $L^3$ each represents, independently at each occurrence, a leaving group;
$R^3$ represents halogeno or $C_{1-4}$ alkyl;

a represents, independently at each occurrence, an integer from 0 to 4;

$X^1$—$X^2$ represents C(O)—CH($Y^1$), C(H)=C($Y^1$), $CH_2$—CH($Y^1$), NH—CH($Y^1$), $CH_2$—C(O), NH—C(O) or CH($Y^1$);

b represents 0 or 1;

$X^3$—$X^4$ represents CH=C($Y^2$), O—CH($Y^2$), NH—CH($Y^2$), O—C(O) or NH—C(O);

c represents an integer from 0 to 10;

Z represents —$SO_2$.NH— or —NH.$SO_2$—;

d represents 0 or 1;

$X^5$—$X^6$ represents $CH_2$—$CH_2$, CH=CH or O—$CH_2$; and $Y^1$ and $Y^2$ independently represent, at each occurrence, H or $C_{1-4}$ alkyl;

or a pharmaceutically acceptable derivative thereof, provided that at least one of the following is the case:

(a) $R^{1a}$ represents $(CH_2)_2$-$L^1$;

(c) $R^{2a}$ represents $(CH_2)_2$-$L^3$.

Preferred compounds of formula I include those in which:

$R^{1a}$ represents $(CH_2)_2$-$L^1$ or the structural fragment

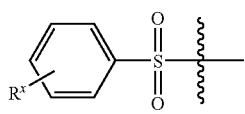

wherein the $R^x$ group, when it represents $N(R^{1b})R^{2b}$, is attached in the 2-, the 3- or, preferably, the 4-position relative to the $S(O)_2$ moiety;

$R^{1b}$ and $R^{2b}$ both represent $(CH_2)_2$-$L^2$;

$R^2$ represents $(CH_2)_2$-$L^3$ or, when $R^x$ represents $N(R^{1b})R^{2b}$, then $R^2$ represents H;

$L^1$, $L^2$ or $L^3$ represents, at each occurrence, Cl, Br or I, or $CH_3SO_2O$ (mesyloxy);

a represents 0;

$X^1$—$X^2$ represents C(O)—CH($Y^1$), C(H)=C($Y^1$) or NH—C(O);

b represents 1;

$X^3$—$X^4$ represents CH=C($Y^2$);

c represents an integer from 0 to 3 (e.g. 0 or 1);

$X^5$—$X^6$ represents CH=CH or O—$CH_2$;

$Y^1$ and $Y^2$ independently represent, at each occurrence, H or $C_{1-2}$ alkyl (e.g. H or methyl).

Preferred compounds of formula I also include compounds of formulae Ia, Ib, Ib', Ic, Ic', Id and Ie:

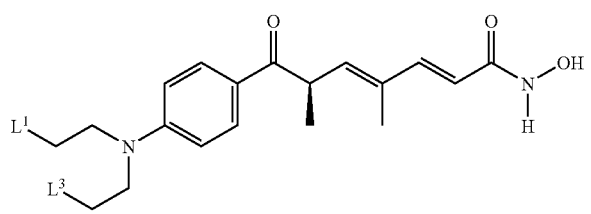
Ia

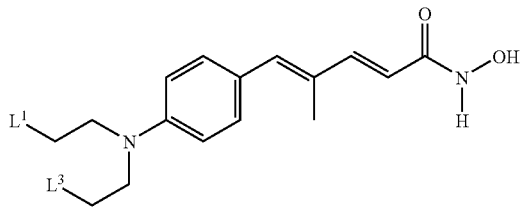
Ib

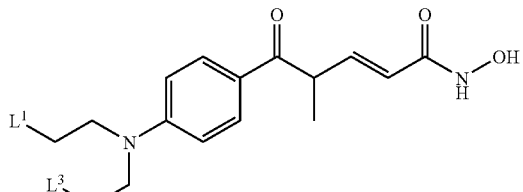
Ib'

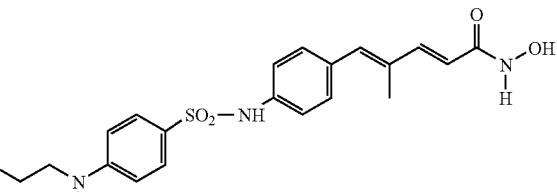
Ic

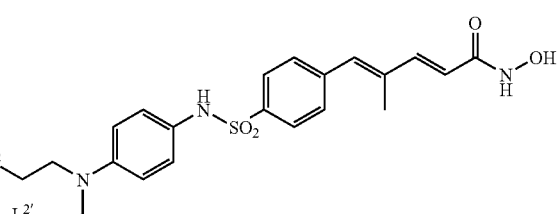
Ic'

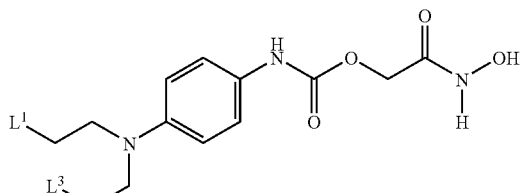
Id

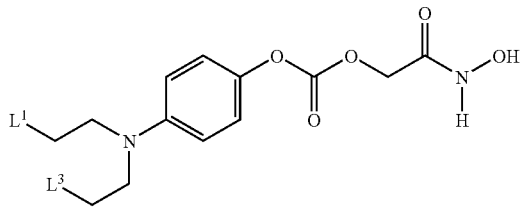
Ie wherein, for each of Ia, Ib, Ib', Ic, Ic' and Id, $L^1$, $L^2$ and $L^3$ are as defined above, and $L^{2'}$ represents a leaving group analogous to $L^2$.

Compounds of formula I (including compounds of formulae Ia, Ib, Ib', Ic, Ic' or Id) may be made in accordance with techniques well known to those skilled in the art, for example as described hereinafter.

According to a further aspect of the invention there is provided a process for the preparation of a compound of formula I, which comprises:

(a) for compounds of formula I in which $L^1$, $L^2$ and/or $L^3$ represents halogeno, halogenation of a corresponding compound of formula II,

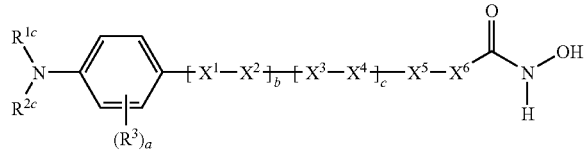

(b) for compounds of formula I in which $L^1$, $L^2$ and/or $L^3$ represents $OS(O)_2R^4$, reaction of a compound of formula II, as hereinbefore defined, with a compound of formula III,

wherein $L^4$ represents a suitable leaving group (e.g. halo or $OS(O)_2R^4$) and $R^4$ is as hereinbefore defined, for example under conditions known to those skilled in the art (e.g. at sub-ambient (e.g. −10 to +5° C.) in the presence of a suitable solvent (e.g. dichloromethane or acetonitrile) and an appropriate base (e.g. a tertiary amine such as triethylamine));

(c) for compounds of formula I in which either $L^1$ and $L^3$ both represent chloro, or in which $R^{2a}$ is other than $(CH_2)_2$-$L^3$ and $N(R^{1b})R^{2b}$ represents $N((CH_2)_2Cl)_2$, reaction of a compound of formula IVA or of formula IVB

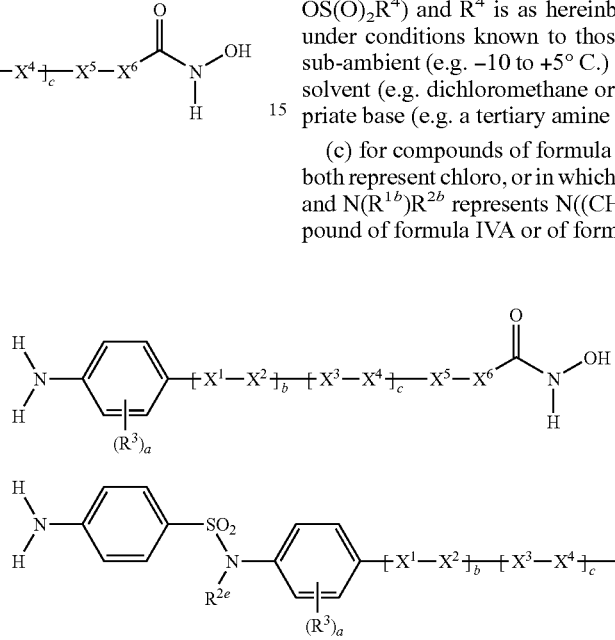

wherein $R^{2e}$ takes the same definition as $R^{2a}$ above, except that, it does not represent $(CH_2)_2$-$L^3$, and $R^3$, $X^1$ to $X^6$, a, b and c are as hereinbefore defined, with two or more equivalents of chloroacetaldehyde, either in the presence of, or followed by the addition of, a suitable reducing agent (e.g. sodium borohydride, sodium cyanoborohydride or, alternatively, hydrogen in combination with an appropriate catalyst, such as palladium on carbon), for example under conditions known to those skilled in the art;

(d) reaction of a compound of formula V,

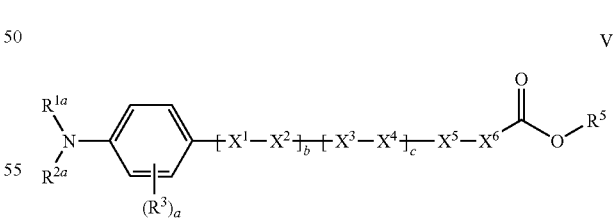

wherein $R^5$ represents $C_{1-4}$ alkyl and $R^{1a}$, $R^{2a}$, $R^3$, $X^1$ to $X^6$, a, b and c are as hereinbefore defined, with hydroxylamine, or a suitable salt thereof (e.g. hydroxylamine hydrochloride), for example under conditions known to those skilled in the art (e.g. in the presence of a suitable solvent (such as water) and an appropriate base (such as potassium hydroxide)); or (e) reaction of a compound of formula V, wherein $R^5$ represents hydrogen and $R^{1a}$, $R^{2a}$, $R^3$, $X^1$ to $X^6$, a, b and c are as hereinbefore defined, with a coupling agent such as diethyl wherein $R^{1c}$ represents $C_{1-4}$ alkyl (which latter group is optionally substituted by one or more substituents selected from halogeno and aryl), aryl, $(CH_2)_2$—OH or the structural fragment

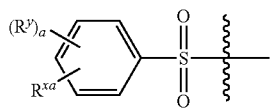

wherein $R^x$ represents H or $N(R^{1d})R^{2d}$,
$R^{1d}$ and $R^{2d}$ independently represent $C_{1-4}$ alkyl (which latter group is optionally substituted by one or more substituents selected from halogeno and aryl), aryl or $(CH_2)_2$—OH,
$R^{2a}$ represents H, $C_{1-4}$ alkyl (which latter group is optionally substituted by one or more substituents selected from halogeno and aryl), aryl or $(CH_2)_2$—OH,
and $R^y$, $R^3$, $X^1$ to $X^6$, a, b and c are as hereinbefore defined, provided that at least one of $R^{1c}$, $R^{2c}$, $R^{1d}$ and $R^{2d}$ represents $(CH_2)_2$—OH, for example under conditions known to those skilled in the art (e.g. reaction of the compound of formula II under suitable conditions with a halogenating agent such as a hydrohalic acid (e.g. concentrated hydrochloric or hydrobromic acid; optionally in the presence of a suitable catalyst, such as a zinc halide or hexamethylphosphoramide), a phosphorous halide or oxyhalide (e.g. $PCl_3$, $PCl_5$, $PBr_3$ or $P(O)Cl_3$), a thionyl halide (e.g. $SOCl_2$ or $SOBr_2$), a mixture of trialkyl or triaryl phosphine and halogen (e.g. a mixture of $Ph_3P$ with $Cl_2$, $Br_2$ or $I_2$), $Me_2SBr_2$ (prepared from $Me_2S$ and $Br_2$) or a mixture of triphenylphosphine and $CCl_4$);

chlorophosphate, oxalyl chloride, ClCO₂Et or ClCO₂ⁱPr, followed by reaction with hydroxylamine, or a suitable salt thereof (e.g. hydroxylamine hydrochloride), in the presence of a suitable solvent (such as dry THF) and an appropriate base (such as triethylamine). In such a case, diethyl chlorophosphate has been found to be a particularly effective coupling agent.

Figure 4:
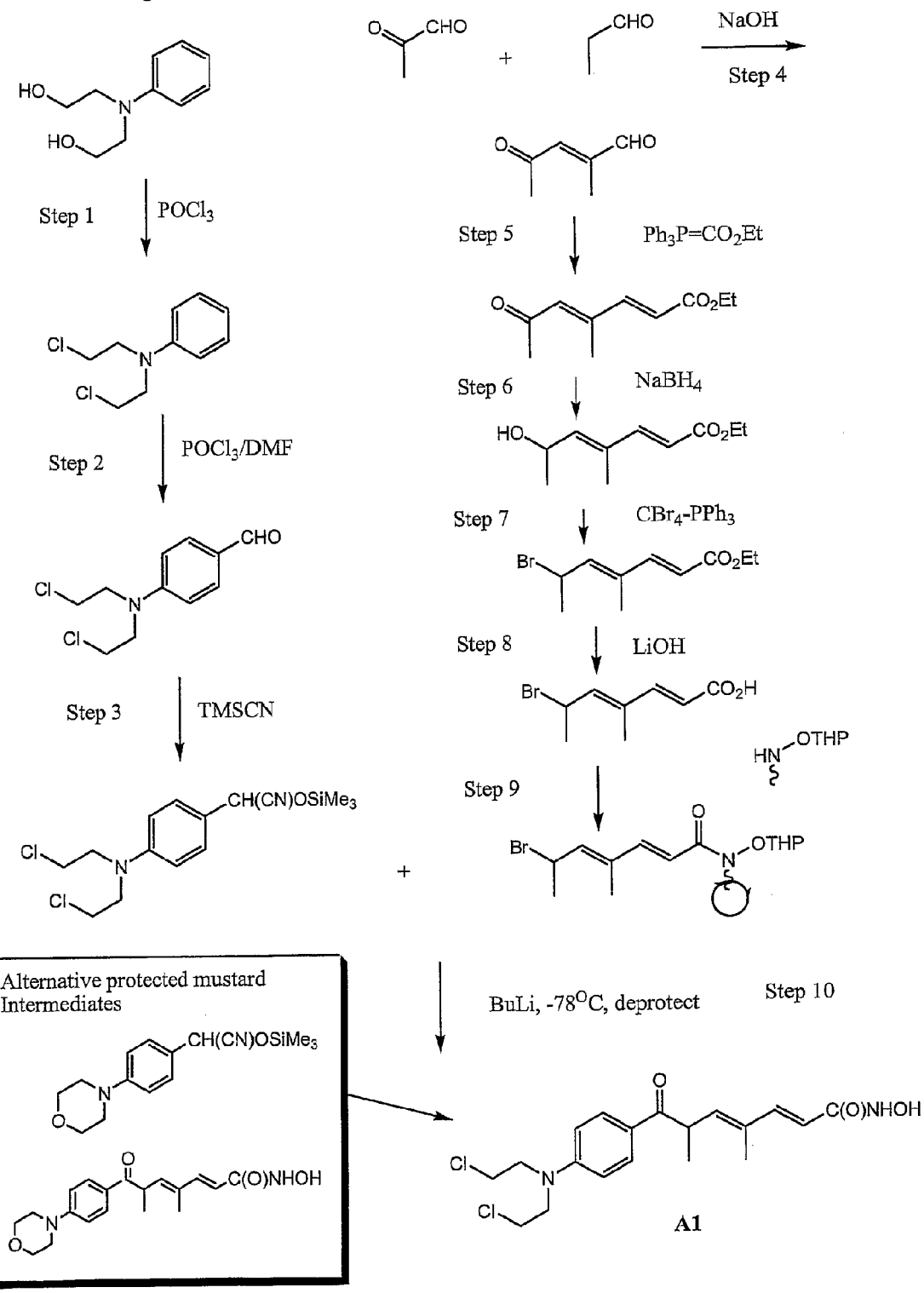
Figure 4A:
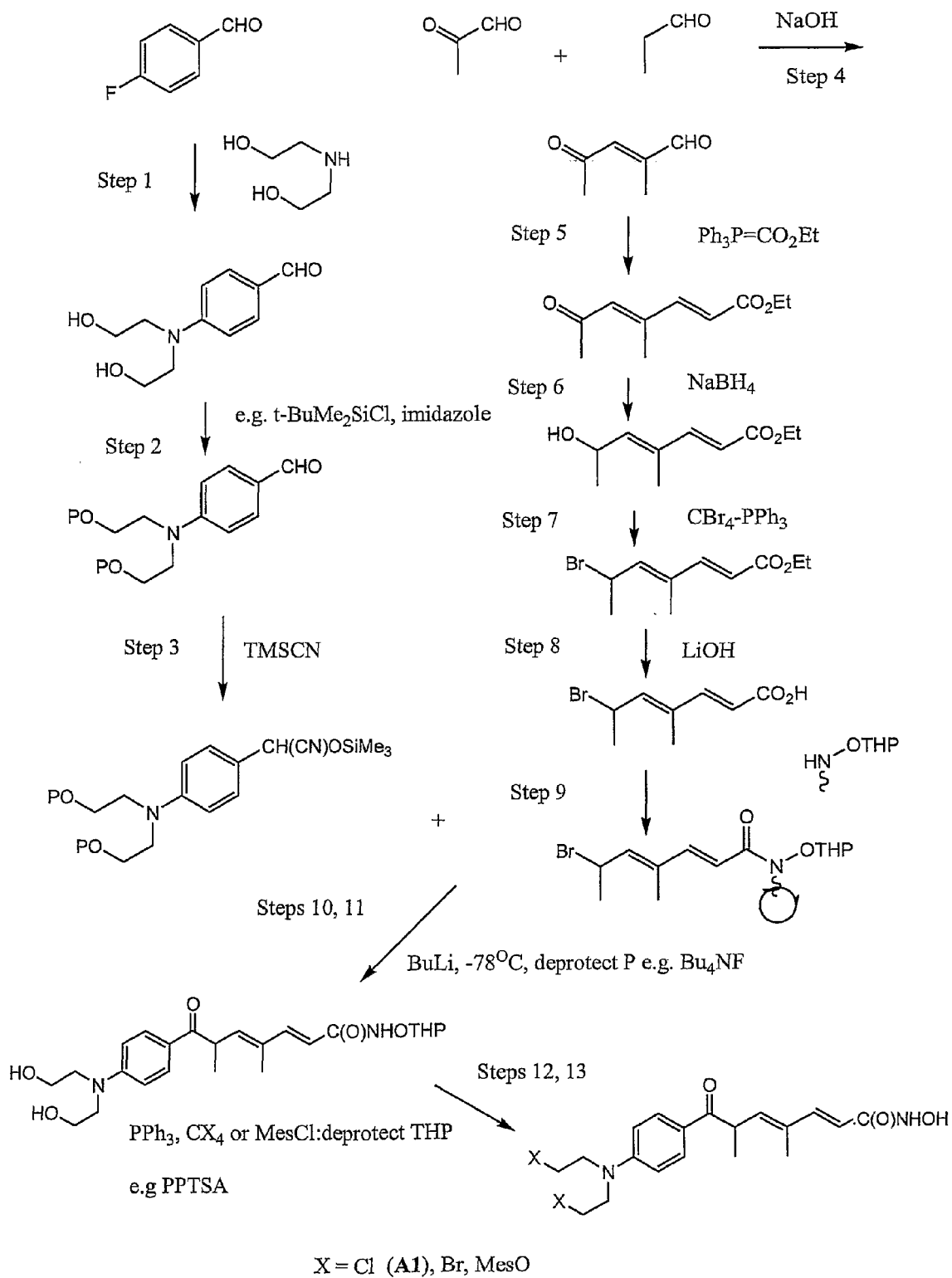
Figure 5:
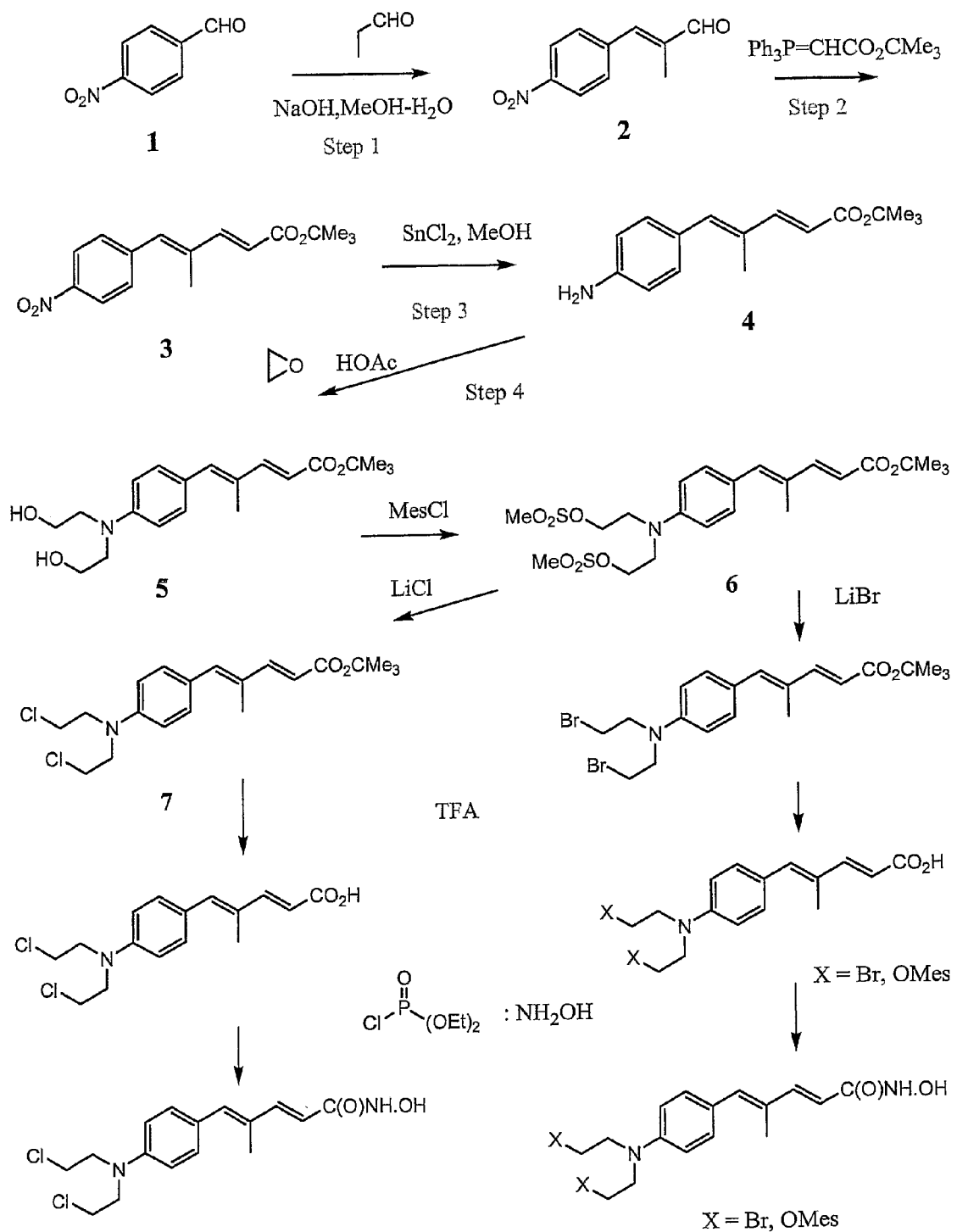

Further routes which may be useful for synthesizing the compounds of the first aspect of the invention are shown in FIG. 3 and FIGS. 4 to 7. FIGS. 3, 4 and 4A show a route for the synthesis of ketone hydroxamate compounds of formulae Ia, FIG. 5 a route for the synthesis of hydroxamate compounds of formulae Ib, FIGS. 6 and 6A a route for the synthesis of sulfonamide hydroxamate compounds of formulae Ic, FIG. 6B a route for the synthesis of a comparative sulfonamide hydroxamate compound, and FIG. 7 a route for the synthesis of carbamate compounds of formulae Id.

Compounds of formula II in which either $R^{1c}$ and $R^{2c}$ both represent $(CH_2)_2$—OH, or in which $R^{2c}$ takes the same definition as $R^{2e}$ above and $N(R^{1b})R^{2b}$ represents $N((CH_2)_2OH)_2$, may be prepared by reaction of a compound of formula IVA or IVB, as hereinbefore defined, with two equivalents of:
(a) ethylene oxide; or
(b) 2-bromoethanol or 2-chloroethanol,
in each instance under conditions that are known to those skilled in the art.

Compounds of formulae IVA and IVB may be prepared by reaction of a compound of formula VIA or VIB, respectively,

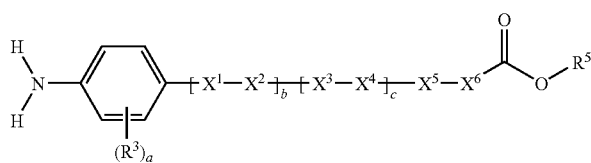

VIA

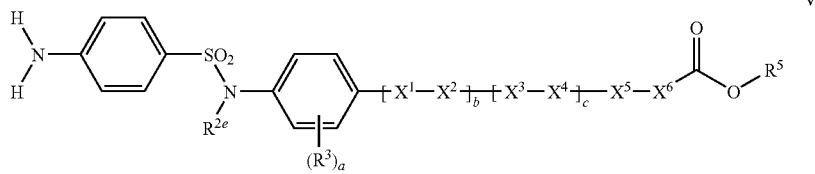

VIB wherein $R^{2e}$, $R^3$, $R^5$, $X^1$ to $X^6$, a, b and c are as hereinbefore defined, with hydroxylamine or a suitable salt thereof, for example under conditions know to those skilled in the art (e.g. those described in respect of process step (d) above).

Compounds of formula V may be made by analogy with processes know to those skilled in the art (e.g. those described *Bioorg. Med. Chem. Lett.* 14, 2477 (2004), the disclosures of which document are hereby incorporated by reference). For example, compounds of formula V in which $X^5$—$X^6$ represents CH═CH may be prepared by reaction of a compound of formula VII,

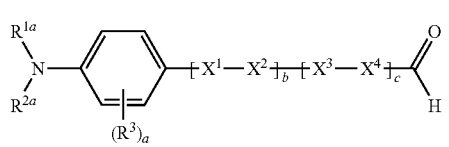

VII wherein $R^{1a}$, $R^{2a}$, $R^3$, $X^1$ to $X^4$, a, b and c are as hereinbefore defined, with a compound of formula VIII,

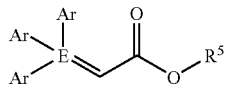

VIII wherein each Ar represents aryl (such as phenyl), E represents a phosphorous or arsenic atom and $R^5$ is as hereinbefore defined, for example under conditions know to those skilled in the art (e.g. at sub-ambient temperature (such as from −78 to +10° C.) in the presence of a suitable solvent (such as tetrahydrofuran (THF)) and, optionally, an appropriate base (such as $K_2CO_3$ or n-butyllithium)).

Compounds of formulae VIA and VIB may be prepared by analogy with the methods described for compounds of formula V.

Compounds of formula VII may be prepared by analogy with methods known to those skilled in the art. For example, compounds of formula VII in which $[X^1$—$X^2]_b$—$[X^3$—$X^4]_c$— represents $C(H)$═$C(CH_3)$— may be prepared by reaction of a compound of formula IX,

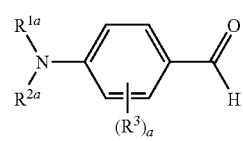

IX wherein $R^{1a}$, $R^{2a}$, $R^3$ and a are as hereinbefore defined, with ethanal (acetaldehyde) under aldol condensation conditions known to those skilled in the art (e.g. in the presence of a suitable base (such as sodium ethoxide) and an appropriate solvent (such as THF)).

Compounds of formulae III, VIII, IX and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl) group(s) in compounds defined herein may be converted to other claimed substituents using techniques well known to those skilled in the art. For example, phenyl may be halogenated to give halophenyl, etc.

The skilled person will also appreciate that various standard substituent or functional group interconversions and transformations within certain compounds of formula I will provide other compounds of formulae I. For example, alkane- or arene-sulfonato may be converted to halogeno.

The compounds of the invention may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for amino include benzyl, sulfonamido (e.g. benzenesulfonamido), tert-butyloxycarbonyl, 9-fluorenyl-methoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore. Protecting groups may be removed in accordance with techniques which are well known to those skilled in the art and as described hereinafter.

The use of protecting groups is fully described in "Protective Groups in Organic Chemistry", edited by J. W. F. McOmie, Plenum Press (1973), and "Protective Groups in Organic Synthesis", $3^{rd}$ edition, T. W. Greene & P. G. M. Wutz, Wiley-Interscience (1999).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Some of the intermediates referred to hereinbefore are novel. According to a further aspect of the invention there is thus provided: (a) a compound of formula II, as hereinbefore defined, or a protected derivative thereof; and (b) a compound of formula V, or a protected derivative thereof.

Similar processes may be used to prepare comparative compounds. Thus, according to a further aspect of the invention there is provided such a compound of formula:

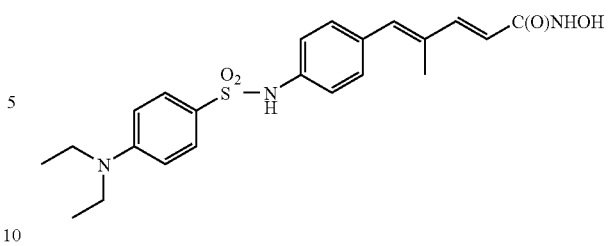

A second aspect of the invention provides a pharmaceutical formulation comprising a compound according to the first aspect of the invention in admixture with a pharmaceutically acceptable adjuvant, diluent or carrier.

Preferably, the formulation is a unit dosage containing a daily dose or unit, daily subdose or an appropriate fraction thereof, of the active ingredient.

The compounds of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds of the invention can be administered alone but will generally be administered in admixture with a suitable pharmaceutical excipient diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds of the invention will usually be from 1 to 1000 mg per adult (i.e. from about 0.015 to 15 mg/kg), administered in single or divided doses.

Thus, for example, the tablets or capsules of the compound of the invention may contain from 1 mg to 1000 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains at least 1 mg of a compound of the invention for delivery to the patient. It will be appreciated that he overall daily dose with an aerosol will vary from patient to patient, and may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the compounds of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or topical administration of the compounds of the invention is the preferred route, being the most convenient. In circumstances where the recipient suffers from a swallowing disorder or from impairment of drug absorption after oral administration, the drug may be administered parenterally, e.g. sublingually or buccally.

The compound of the invention may be further presented in the form of a 'prodrug'. The term "prodrug" as used in this application refers to a precursor or derivative form of a pharmaceutically active substance that is less cytotoxic to tumour cells compared to the parent drug and is capable of being enzymatically activated or converted into the more active parent form (see, for example, D. E. V. Wilman "Prodrugs in Cancer Chemotherapy" *Biochemical Society Transactions* 14, 375-382 (615th Meeting, Belfast 1986) and V. J. Stella et al. "Prodrugs: A Chemical Approach to Targeted Drug Delivery" *Directed Drug Delivery* R. Borchardt et al. (ed.) pages 247-267 (Humana Press 1985)).

An embodiment of this aspect of the invention is wherein the pharmaceutical composition comprises one or more further anticancer agents.

Examples of such anticancer agents include tyrosine kinase inhibitors (imatinib, gefitinib, and others); DNA methyltransferase inhibitors (5-aza-2'-deoxycytidine, 5-azacytidine, and others); tamoxifen; aromatase inhibitors (anastrozole, letrozole, exemestane, and others); fulvestrant progestogens (megestrol acetate, medroxyprogesterone acetate, gestonorone caproate, norethisterone, and others); anti-androgens (cyproterone acetate, flutamide, bicalutamide, and others); luteinising hormone releasing hormone analogues (goserelin, leuprorelin, buserelin, and others); oestrogens (ethinylestradiol, diethylstilbestrol, and others); anthracyclines (doxorubicin, epirubicin, daunorubicin, idarubicin, aclarubicin, and others); topoisomerase I inhibitors (etoposide, teniposide, and others); topoisomerase II inhibitors (irinotecan, topotecan, and others); fluoropyrimidines (5-fluorouracil, FUdR, tegafur, capecitabine, gemcitabine, raltitrexed, and others); alkylating agents (cyclophosphamide, ifosfamide, chlorambucil, thiotepa, busulfan, carmustine, mustine, estramustine, lomustine, treosulfan, melphalan, dacarbazine, procarbazine, and others); methotrexate; hydroxyurea; platinum compounds (cisplatin, carboplatin, oxaliplatin, and others); taxanes (paclitaxel, docetaxel, and others); purine analogues (mercaptopurine, pentostatin, cytarabine, fludarabine, thioguanine, cladribine, and others); vinca alkaloids (vincristine, vinblastine, vinorelbine, vindesine, and others); proteasome inhibitors (bortezomib, lactacystin, MG-132, and others); retinoids (ATRA, bexarotene, tretinoin, isotretinoin, and others); immunosuppressant and immunomodulating drugs (azathioprine, tacrolimus, ciclosporin, and others).

A third aspect of the invention is a compound according to the first aspect of the invention or a pharmaceutical composition according to the second aspect of the invention for use in medicine.

The compounds of the invention may be of use in the prevention or treatment of a range of conditions or diseases in which inhibition of histone deacetylase by a compound of the invention can prevent, inhibit, or ameliorate the pathology and/or symptomatology of the condition or disease, enhance or otherwise augment the activity of any other agent used to prevent or treat the condition or disease; sensitise the condition or disease to any preventive or therapeutic agent. The condition or disease may be caused by or associated with abnormal cell proliferation.

For example, the compounds of the invention may be of clinical use in the prevention or treatment of cancer.

The compounds of the invention may also be used to prevent or treat premalignant haematological conditions e.g. myelodysplasia and myelodysplastic syndromes.

The compounds of the invention may also be used to prevent or treat haemoglobinopathies, e.g. sickle cell anaemia and β-thalassaemia (there are 240 million humans worldwide that are heterozygotic for the alleles associated with these disorders). The relevant alleles are actively selected for by *Plasmodium vivax* and *P. falciparum* malaria infections (for which compounds of the invention may also be used to treat).

The compounds of the invention may also be used to prevent or treat microbial infections e.g. superficial and invasive fungal infections (*Candida* sp., *Aspergillus* sp., coccidioidomycosis, histoplasmosis and others), or parasitic infections e.g. malaria or other protozoal infections e.g. *Pneumocystis carinii; Toxoplasma gondii*.

The compounds of the invention may also be used to prevent or treat neurodegenerative diseases, both inherited (e.g. Huntington's disease) and acquired (e.g. Alzheimer's disease), hyperproliferative diseases (e.g. keloid, psoriasis hypertrophic cardiomyopathy, hepatic and biliary fibrosis) or connective tissue diseases (e.g. systemic lupus erythematosus), neovascular diseases, e.g. of the eye (e.g. diabetic retinopathy, neovascular glaucoma, corneal neovascularisation), diabetes mellitus.

The compounds of the invention may also be used to prevent or treat graft or stent occlusion (e.g. HDACi impregnated stents, coronary artery bypass grafts), as chemoprevention in high risk groups (e.g. cancer associated with familial polyposis coli, ulcerative colitis or BRCA1 or BRCA2 gene mutations) or in the prevention of premature labour and parturition.

The compounds of the invention may also be used to prevent or overcome drug resistance e.g. imatinib in Philadelphia chromosome positive chronic myelogenous myeloid leukaemia; anthracyclines and other cytotoxic chemotherapy drugs; endocrine therapies in hormone responsive cancers (tamoxifen and aromatase inhibitors and fulvestrant in breast cancer, anti-androgens and luteinising hormone releasing hormone analogues in prostate cancer).

A fourth aspect of the invention is the use of a compound according to the first aspect of the invention or a pharmaceutical composition according to the second aspect of the invention in the manufacture of a medicament for the prevention or treatment of cancer.

By 'cancer' we include both tumorous and non-tumorous cancers. We include primary and/or locally advanced and/or metastatic solid tumours, including but not limited to cancers of the breast, upper aerodigestive tract, endocrine system including thyroid; adrenal gland, parathyroid, carcinoid and pancreatic neuroendocrine tumours, lung, oesophagus, stomach, pancreas, liver, gall bladder and hepatobiliary system, small intestine, colorectal, ovarian, bladder, prostate, gynaecologic tumours (vulva, vagina, cervix, endometrium, uterine, fallopian tubes), testis, penis and urethra, renal, central nervous system, skin (basal and squamous cell carcinomas and melanoma), sarcomas of soft tissue and bone, mesothelioma, developmental cancers such as testicular or ovarian germ cell tumours and teratomas, and gestational trophoblastic tumours including hydatidiform moles and choriocarcinomas, primary and metastatic bone tumours, intraocular melanomas, and solid tumours of childhood.

We also include haematological malignancies including but not limited to acute and chronic leukaemias (acute myelogenous leukaemia, acute lymphoblastic leukaemia, acute promyelocytic leukaemia, chronic myelogenous leukaemia, chrome lymphocytic leukaemia, hairy cell leukaemia) lymphomas (Hodgkin's disease and non-Hodgkin's lymphomas, cutaneous and peripheral T-cell lymphomas), and plasma cell tumours including multiple myeloma.

The cancer may be a tumorous or non-tumorous cancer.

An embodiment of this aspect of the invention is wherein said medicament is administered concurrently or sequentially with one or more further anticancer agent. Examples of such anticancer agents are provided above in connection with the second aspect of the invention.

Any publications referred to herein are hereby incorporated by reference.

The invention will now be described in more detail by reference to the following non-limiting Figures and Examples.

FIG. 1: Structure of TSA and lysine chain and acetyl group of the histone substrate FIG. 2: Structure of TSA and two major metabolites FIGS. 3 to 8: Further routes which may be useful for synthesizing the compounds of the first aspect of the invention FIG. 9: HDAC assay using the Fluor de Lys assay kit FIG. 10: In vitro cellular growth inhibition in MCF-7 cells using the SRB assay kit FIG. 11: HDAC1 irreversibility assay using the Fluor de Lys assay kit. Two independent experiments are shown FIG. 12: Irreversibility of growth inhibition using the SRB assay kit.

Figure 13:

FIG. 13: C1A inhibits pRb & cyclin D and induces H4 hyperacetylation at ≧10× [TSA]

Figure 14:
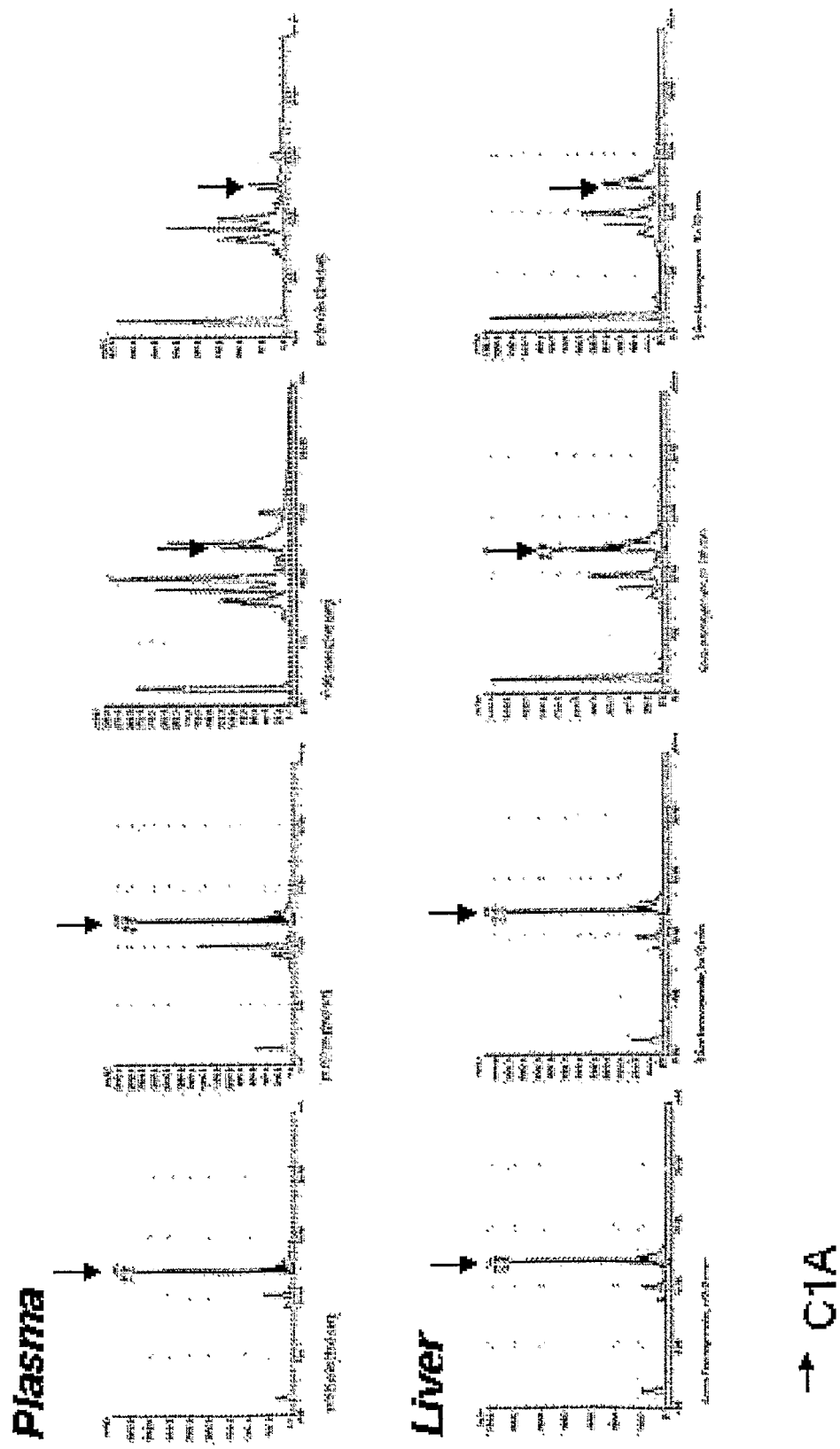

FIG. 14: Pharmacokinetics of C1A in after 80 mg/kg i.v. injection in Balb/c mice: C1A is stable in vivo FIG. 15: C1A appears (n=1) to be efficacious in vivo FIG. 16: Early i.p. pharmacokinetic studies in vivo: C1A is stable in vivo in the mouse FIG. 17: TSA is rapidly metabolised in vivo

EXAMPLE 1

Determining the MPHis Activity of Compounds of the Invention

1. In vitro Radioactive Assay for Total Histone Deacetylase Inhibition

Histone deacetylase inhibitory activity can be measured as described by Vigushin et al. (2001) *Clin. Cancer Res.* 7, 971-976 based on methods published by Taunton et al. (1995) *Science* 272, 408-411 and Emiliani et al. (1998) *Proc. Natl. Acad. Sci.* USA 95, 2795-2800.

Briefly, the assay begins by incubating histone deacetylase enzymes contained in a nuclear extract from the HeLa human cervical adenocarcinoma cell line with a compound of the invention followed by addition of a radiolabelled substrate. The substrate is a synthetic peptide corresponding to histone H4 (amino acids 14-21) that has been chemically acetylated on lysine residues with sodium [$^3$H]acetate according to the method published by Taunton et al. (1995) Science 272, 408-411. Released [$^3$H]acetic acid (a measure of histone deacetylase activity) is then extracted with ethyl acetate and quantified in a scintillation counter. The concentration of a compound of the invention that inhibits histone deacetylase activity by 50% (i.e. $IC_{50}$) can then be determined by repeating the assay with a range of different concentrations of compound. Each assay is performed in duplicate with control samples in triplicate for accuracy.

1.1 HeLa Cell Nuclear Extract

HeLa cell nuclear extract is prepared according to the method of Dignam et al. (1983) Nucleic Acids Res. 11, 1475-1489. HeLa human cervical adenocarcinoma cells are grown at 37° C. in DMEM medium containing 5% foetal calf serum to a concentration of $5 \times 10^5$ cells per ml prior to harvesting. Cells were then harvested by centrifugation for 10 minutes at 2,000 rpm in a Sorvall HG4L rotor. The cell pellet was resuspended in 5 volumes of cold phosphate buffered saline, collected by centrifugation at 4° C. and all subsequent manipulations are performed at 4° C. Cells are suspended in 5 packed cell volumes of 10 mM HEPES (pH 7.9 at 4° C.), 1.5 mM $MgCl_2$, 10 mM KCl and 0.5 mM DTT and allowed to equilibrate for 10 minutes. The cells are pelleted by centrifugation as above, resuspended in 2 packed cell volumes of the same buffer and then lysed by 10 strokes of a glass Dounce homogeniser. The homogenate is centrifuged as before and the pellet then centrifuged for 20 minutes at 25,000×g in a Sorvall SS34 rotor to remove residual cytoplasmic material, yielding crude nuclei. Crude nuclei from $10^9$ cells are resuspended in 3 ml of 20 mM HEPES (pH 7.9), 25% (v/v) glycerol, 420 mM NaCl, 1.5 mM $MgCl_2$, 0.2 mM EDTA, 0.5 mM phenylmethylsulfonyl fluoride (PMSF) and 0.5 mM DTT with a glass Dounce homogeniser (10 strokes). After stirring gently with a magnetic stirrer for 30 minutes, the suspension is centrifuged for 30 minutes at 25,000×g (Sorvall SS34 rotor). The supernatant is dialysed against 50 volumes of 20 mM HEPES (pH 7.9), 20% (v/v) glycerol, 100 mM KCl, 0.2 mM EDTA, 0.5 mM PMSF and 0.5 mM DTT for 5 hours and the dialysate then centrifuged at 25,000×g for 20 minutes (Sorvall SS34 rotor). The supernatant, designated the nuclear extract, is then snap frozen in liquid nitrogen and stored at −80° C. The protein concentration measured by Bradford assay is ~10 mg/ml and ~50 mg of protein is obtained from $10^9$ cells.

1.2 Acetylation of Histone H4 Peptide with [$^3$H]Acetate

A peptide corresponding to amino-terminal residues 14-21 of histone H4 (GAKRHRKV) is synthesised in an automated peptide synthesiser (ABI 433; Applied Biosystems, Cheshire, UK), purified by reverse phase high performance liquid chromatography (HPLC), and lyophilised. The peptide should be >95% pure by reverse phase HPLC, mass spectrometry and capillary electrophoresis. All subsequent steps are performed in a fume hood. To 1 mg of the lyophilised peptide in a 2 ml screw top amber glass vial is added 500 µl (12.5 mCi) of sodium [$^3$H]acetate (9.9 Ci/mmol, 25 mCi/ml in ethanol; ICN Pharmaceuticals, Basingstoke, UK). Then 20 µl of a freshly prepared solution of 0.24 M benzotriazol-1-yloxytris(dimethylamino)phosphonium hexafluorophosphate (BOP reagent; Sigma-Aldrich, Gillingham, UK) and 0.2 M triethylamine in acetonitrile is added, the reaction vial is capped, and the labelling mixture incubated on a rotating platform overnight at room temperature. The mixture is then concentrated to dryness under reduced pressure and the residue dissolved in 1 ml TEN buffer [50 mM Tris (pH 8.0), 150 mM NaCl, 5 mM EDTA].

After centrifugation at 14,000×g for 15 seconds at room temperature, the supernatant containing [$^3$H]acetate-labelled histone H4 peptide is purified by gel filtration on Sephadex G-25 (PD10 column; Amersham Biosciences UK Limited, Buckinghamshire, UK). After equilibrating with 10 column volumes of TEN, the supernatant is loaded onto the column and then eluted with TEN. 0.5 ml fractions are collected and the radioactivity in each quantified by liquid scintillation counting. After the column void volume, the [$^3$H]acetate-labelled histone H4 peptide elutes first followed by free unincorporated label ([$^3$H]acetic acid). Eluates containing the purified radiolabelled peptide are pooled, divided into aliquots and stored at −70° C. until use.

1.3 In Vitro Histone Deacetylase Assay

Histone deacetylase inhibition by compounds of the invention is assayed as described in Vigushin et al. (2001) *Clin. Cancer Res.* 7, 971-976 based on methods published by Taunton et al. (1995) *Science* 272, 408-411 and Emiliani et al. (1998) *Proc. Natl. Acad. Sci.* USA 95, 2795-2800. HeLa cell nuclear extract prepared according to Dignam et al. (1983) *Nucleic Acids Res.* 11, 1475-1489 is used as a source of histone deacetylase enzymes. The substrate is a synthetic peptide corresponding to amino acids 14-21 of histone H4 and chemically acetylated on lysine residues with sodium [$^3$H]acetate as described by Taunton et al. (1995) Science 272, 408-411. A stock solution in dimethyl sulfoxide (DMSO) is prepared for each compound of the invention to be tested and trichostatin A as a positive control. Stock solutions are diluted in DMSO to give a range of 100× working solutions.

The assay is performed in a final reaction volume of 200 µl. To each tube is added 40 µl of 5×HDAC buffer [50 mM Tris (pH 8.0), 750 mM NaCl, 50% (v/v) glycerol, 1 mM PMSF], 4 µl (40 µg total protein) HeLa cell nuclear extract, 2 µl 100× inhibitor in DMSO or 2 µl DMSO as a negative control, and water to a total of 199 µl. After mixing by vortex and brief centrifugation (14,000×g for 5 seconds at room temperature), the reaction mixture is incubated for 30 minutes at room temperature. The assay is then initiated by addition of 1 µl (37 kBq) of [$^3$H]acetate-labelled histone H4 peptide substrate. After brief vortex and centrifugation as above, the reaction mixture is incubated for 60 minutes at room temperature. Fifty µl of a quenching solution [1 M HCl/0.16 M acetic acid] is then added to stop the reaction. The released [$^3$H]acetate in each assay reaction is extracted into 600 µl ethyl acetate. After mixing by vortex, the organic and aqueous phases are separated by centrifugation (14,000×g for 1 minute at room temperature). Duplicate 200 µl aliquots of the upper organic phase are transferred into separate scintillation vials each containing 5 ml scintillant (Bionic Fluor; Canberra Harwell Ltd., Didcot, UK) and the radioactivity in each measured by β-scintillation counting.

An initial assay is performed to establish the range of activity of each compound of the invention. The assay is then repeated using four log dilutions in range according to the expected potency for each test compound. The concentration of each compound of the invention that inhibits total histone deacetylase enzyme activity by 50% ($IC_{50}$) is determined graphically in each case using non-linear regression analysis to fit inhibition data to the appropriate dose-response curve (GraphPad Prism Version 4.0; GraphPad Software Inc., San Diego, Calif.). Each test compound is assayed in duplicate whilst positive and negative control samples are assayed in triplicate.

1.4 Fluorometric HDAC Inhibition Assay

Histone deacetylase inhibition by compounds of the invention is assayed by a commercial fluorescent assay kit (BIOMOL—AK-500). 10 mM stock solutions of compounds of the invention prepared in DMSO are aliquoted and frozen at −20° C. For each assay, a vial of the drug solution is thawed to prepare dilutions of drug in DMSO; the remaining drug is discarded. Working solutions of the assay reagents are prepared according to the manufacturers instructions. For the assay, 10 µl of ×5 concentrations of drug (in triplicate) or HDAC assay buffer is added to 15 µl of dilute HeLa nuclear extract (BIOMOL; D1409) and 25 µl of (2×) Fluor-de-Lys substrate in a micro titre plate (Perkin Elmer # 6005270, Optiplate-96 Black microplate) and thoroughly mixed. TSA is used as control. The reactions are allowed to proceed for 10 min and then stopped by addition of 50 µl of dilute Fluor-de-Lys developer solution. The reaction mixtures are then incubated at room temperature for 15 min and fluorescence is read on a Victor multi-well Fluorescence plate reader at an excitation wavelength of 355 nm and emission wavelength of 460 nm.

1.5 Data Analysis

To obtain a calibration curve, 50 µl aliquots of deacetylated standards prepared in HDAC assay buffer according to the manufacturer's instructions are mixed with 50 µl of diluted Fluor-de-Lys developer solution and incubated for 10 min at room temperature. The fluorescence is measured as above. A plot of arbitrary fluorescence units (AFU) against deacetylated standard concentration in µM is made. The slope and intercept are determined and used for conversion of inhibitor data AFU into velocity of reaction (V, µM/min). To obtain half-maximal inhibition ($EC_{50}$), molar concentrations of drug are plotted against V and the $EC_{50}$ is determined from the sigmoid dose response using the GraphPad Prism software.

2. In Vitro Assay for Irreversible Histone Deacetylase 1 Inhibition

Reversibility of HDAC1 inhibition by the compounds of the invention can be analysed based on a method published by Furumai et al. (2001) *Proc. Natl. Acad. Sci.* USA 98, 87-92.

2.1 Immunoprecipitation of HDAC1

HDAC1 is immunoprecipitated from HeLa cell nuclear extract prepared according to Dignam et al. (1983) Nucleic Acids Res. 11, 1475-1489. To 1 mg of HeLa cell nuclear extract in 1 ml 20 mM HEPES (pH 7.9), 20% (v/v) glycerol, 100 mM KCl, 0.2 mM EDTA, 0.5 mM PMSF and 0.5 mM DTT is added 10 µg of rabbit polyclonal IgG anti-human HDAC1 antibody (#06-720; Upstate Ltd., Milton Keynes, UK) or normal rabbit IgG (Sigma-Aldrich, Gillingham, UK) as a negative control. Each reaction mixture is incubated on a rotating platform at 4° C. for 2 hours. Immune complexes are then captured by adding 40 µl of a washed 50% (v/v) Protein A-Sepharose bead slurry in phosphate buffered saline to each reaction and incubating on a rotating platform at 4° C. for 1 hour. The beads bound HDAC1 immune complexes are collected by pulse centrifugation (14,000×g for 5 seconds at 4° C.), washed 3 times with 1 ml ice cold phosphate buffered saline, and then once with 1 ml of HD buffer [20 mM Tris (pH 8.0), 150 mM NaCl, 10% (v/v) glycerol and complete protease inhibitor mixture (Roche Diagnostics Ltd., East Sussex, UK)]. After removing the supernatant, beads are resuspended in a 50% slurry of HD buffer at 4° C.

2.2 Reversibility of HDAC1 Inhibition

Beads bound HDAC1 slurry is used as the source of HDAC activity in an in vitro HDAC inhibition assay. The substrate is a synthetic peptide corresponding to amino acids 14-21 of histone H4 and chemically acetylated on lysine residues with sodium [$^3$H]acetate as described in 1.2 above. A stock solution in dimethyl sulfoxide (DMSO) is prepared for each compound of the invention to be tested, trichostatin A as a positive control for reversible HDAC1 inhibition, and trapoxin B as a positive control for irreversible HDAC1 inhibition. Stock solutions are diluted in DMSO to give a range of 100× working solutions.

The assay is performed in a final reaction volume of 200 µl. To each tube in duplicate is added 40 µl of 5× HDAC buffer [50 mM Tris (pH 8.0), 750 mM NaCl, 50% (v/v) glycerol, 1 mM PMSF], 10 µl of HDAC1 conjugated-Protein A-Sepharose bead slurry (5 µl packed beads), 2 µl 100× inhibitor in DMSO or 2 µl DMSO as a negative control, and water to a total of 199 µl. After mixing by vortex and brief centrifugation (14,000×g for 5 seconds at room temperature), the reaction mixture is incubated for 30 minutes at room temperature. One of each duplicate reaction is then washed with 1 ml of 1×HDAC buffer, vortexed, and centrifuged (14,000×g for 5 seconds at room temperature). The supernatant is then decanted and the beads resuspended in 199 µl of 1×HDAC buffer. HDAC1 enzyme activity is then determined in the presence or absence of each drug. The assay is initiated by addition of 1 µl (37 kBq) of [$^3$H]acetate-labelled histone H4 peptide substrate. After brief vortex and centrifugation as above, the reaction mixture is incubated for 60 minutes at room temperature. Fifty µl of a quenching solution [1 M HCl/0.16 M acetic acid] is then added to stop the reaction. The released [$^3$H]acetate in each assay reaction is extracted into 600 µl ethyl acetate. After mixing by vortex, the organic and aqueous phases are separated by centrifugation (14,000×g for 1 minute at room temperature). Duplicate 200 µl aliquots of the upper organic phase are transferred into separate scintillation vials each containing 5 ml scintillant (Hionic Fluor; Canberra Harwell Ltd., Didcot, UK) and the radioactivity in each measured by β-scintillation counting. Percentage inhibition of HDAC1 enzyme activity by each test compound of the invention is then compared before and after removal of the test compound to determine whether the mode of enzyme inhibition is reversible by washing or irreversible.

2.3 Fluorometric Assay for Irreversible HDAC1 Assay Inhibition

The irreversibility of histone deacetylase 1 inhibition by compounds of the invention is assayed by a commercial fluorescent assay kit (BIOMOL—AK-500). 100 µl (0.9 mg) of HeLa nuclear extract (BIOMOL; D1409) is added to 400 µl of HDAC assay buffer and mixed. Immune complexes are formed by further mixing with 10 µg of anti-HDAC1 rabbit polyclonal IgG. The mixture is incubated on a rotating platform at 4° C. for 2 h. Immune complexes are captured by adding 80 µl of 25% of protein A/G PLUS-Agarose beads (Santa Cruz) and incubating on a rotating platform at 4° C. for 1 h. Beads are pelleted by centrifugation at 10000 rpm for 5 min at 4° C. The enzyme-bound beads are washed 3 times with 1 ml ice cold phosphate buffered saline, then wash once with 1 ml of HDAC assay buffer. The supernatant is removed and the beads are re-suspended in 50% slurry of HDAC assay buffer at 4° C.

20× solutions of HDAC inhibitors in DMSO are prepared from 10 mM stock solutions in DMSO. The assay is prepared in Eppendorf's in a final reaction volume of 200 µl. To each tube in Duplicate 10 µl of the 20× inhibitor or DMSO, 20 µl of HDAC1 enzyme slurry, i.e. 10 µl packed beads, and 170 µl of HDAC assay buffer are added. The final concentrations of HDAC inhibitors are 100 µM for compounds of the invention, and 1000 µM for depudecin (control). The mixtures are vortexed and incubated for 30 min at 37° C. in a rocking water bath. The mixtures are centrifuged at 10000 rpm for 5 min at 4° C. and supernatant removed. One set of the Duplicate is washed two times with 1 ml of HDAC assay buffer and the supernatant removed.

2.4 HDAC Assay

25 µl of Fluor-de-Lys substrate is added to the beads (~10 µl) and 15 µl of HDAC assay buffer. The mixture is incubated at 37° C. in a rocking water bath for 10 min. At the end of incubation, 50 µl of Fluor-de-Lys developer is added to the mixture and incubated at room temperature for 15 min. Fluorescence is read on a Victor multi-well fluorescence plate reader at an excitation wavelength of 355 nm and emission wavelength of 460 nm. AFU values are plotted.

3. Sulforhodamine B Cell Proliferation Assay

Stock cultures of MCF-7 and MDA-MB-231 human breast cancer cell lines (American Type Culture Collection, Rockville, Md.) are grown in Dulbecco's Modified Eagle's Medium (DMEM) containing 10% (v/v) foetal calf serum, 2 mM L-glutamine, 100 units/ml penicillin and 100 µg/ml streptomycin at 37° C. in 5% $CO_2$ humidified atmosphere. Cells are counted in a haemocytometer after detachment using 0.25% (w/v) trypsin in Dulbecco's Phosphate Buffered Saline without $Ca^{2+}$ or $Mg^{2+}$ (DPBS) (Sigma-Aldrich, Gillingham, UK) containing 0.02% (w/v) EDTA. Viability is determined by Trypan blue exclusion. For each cell line, cells are seeded in 96-well microtitre plates at optimal densities determined in prior experiments to ensure exponential growth for the duration of the assay. After a 24 hour preincubation, growth medium is replaced with experimental medium containing the test compounds of the invention or trichostatin A as a positive control at final concentrations ranging from $10^{-12}$ M to $10^{-5}$ M in log dilutions and 0.1% (v/v) dimethyl sulfoxide, or growth medium containing 0.1% (v/v) dimethyl sulfoxide as a vehicle control. After 48 hour incubation, cell proliferation is determined using the sulforhodamine B colorimetric assay described by Skehan et al. (1990) *J. Natl. Cancer Inst.* 82, 1107-1112. Briefly, 100 µl of ice cold 40% (w/v) trichloroacetic acid is added to each well and incubated for 1 hour at 4° C. The plate is then rinsed gently with five changes of tap water. To each well is then added 100 µl of 0.4% (w/v) sulforhodamine B in 1% (v/v) acetic acid and incubated for 1 hour at room temperature. The plate is then washed five times with 1% (v/v) acetic acid and allowed to air dry overnight. Bound dye is then solubilised by addition of 100 µl of 10 mM Tris base to each well followed by incubation on a vibrating plate shaker for 30 minutes. Absorbance at 492 nm is then measured on a microtitre plate reader and the results expressed as the mean ±SE for 6 replicates as a % of vehicle control (taken as 100%). The concentration of each compound of the invention that inhibits cell proliferation by 50% ($IC_{50}$) is determined graphically in each case using non-linear regression analysis to fit inhibition data to the appropriate dose-response curve (GraphPad Prism Version 4.0; GraphPad Software Inc., San Diego, Calif.).

Irreversible Sulforhodamine B Proliferation Assay

Sub-confluent MCF-7 cells growing in culture are incubated with 1 or 10 µM concentrations of compounds of the invention. In one set of plates, the cells are incubated with drug continuously for 24 h, 48 h or 72 h. In another set, the cells are washed after 24 h and incubated with fresh media for a further 24 h or 48 h. At the end of the incubation period, the cells are assayed by the Sulforhodamine B assay as above.

4. In Vivo Efficacy and Toxicity Evaluation in MCF-7 Nude Mouse Human Tumour Xenograft Model A stock culture of the MCF-7 human breast cancer cell line (American Type Culture Collection, Rockville, Md.) is grown in complete medium [Dulbecco's Modified Eagle's Medium (DMEM) containing 10% (v/v) foetal calf serum, 2 mM L-glutamine, 100 units/ml penicillin and 100 µg/ml streptomycin] at 37° C. in 5% $CO_2$ humidified atmosphere. Balb/C nu/nu immunodeficient female mice 6-8 weeks of age are maintained in controlled conditions of light, temperature and humidity, and fed a standard diet with water ad libitum. A 17β-estradiol pellet 0.72 mg/60-day release (Innovative Research of America, Sarasota, Fla., USA) is implanted subcutaneously in each animal. MCF-7 cells are counted in a haemocytometer after detachment using 0.25% (w/v) trypsin in Dulbecco's Phosphate Buffered Saline without $Ca^{2+}$ or $Mg^{2+}$ (DPBS) (Sigma-Aldrich, Gillingham, UK) containing 0.02% (w/v) EDTA. In order to induce tumour xenografts, $5 \times 10^6$ MCF-7 cells in 100 µl of complete medium is then administered by subcutaneous injection to each mouse. Tumour growth is monitored twice weekly using a Vernier calliper to measure two perpendicular diameters of palpable tumours. Approximately 60% of the animals will develop tumours. Tumours are allowed to grow until they reach a diameter of ~5 mm (volume of ~62.5 $mm^3$) and tumour bearing mice are then randomised into groups of 12. Each mouse is given a unique identifier (ear tag or microchip). Baseline tumour dimensions and body mass is recorded for each mouse. Groups are then treated with test compound of the invention, trichostatin A as a positive control, or vehicle only. The usual dose is in the range 1-100 mg/kg/day in 50 µl vehicle [usually 10% dimethyl sulfoxide in phosphate buffered saline] administered by intraperitoneal injection daily Monday to Friday for 3 weeks. Tumour dimensions and body mass are recorded twice weekly for each mouse. Tumour response is assessed by comparing the mean ±SE tumour volumes (estimated from the perpendicular diameters at each time point) for each treatment and control group. Mean percentage change in body mass over time is also compared in treated and control groups.

Pharmacokinetic drug and metabolism studies may also be undertaken using the methods disclosed in the methods and examples discussed herein.

EXAMPLE 2

Use of MPHis Compounds as Anticancer Agents

A patient having a tumorous or non-tumorous cancer is administered a therapeutically appropriate quantity of a MPHi compound according to the first aspect of the invention. The treatment regime will necessarily vary from patient to patient and from cancer to cancer, as would be appreciated by a physician.

EXAMPLE 3

Synthesis of (E,E)-4-methyl-5-{4-[4-bis-(2-chloroethylamino)phenyl]-sulfonamido}penta-2,4-dienoic acid N-hydroxyamide [C1-A]

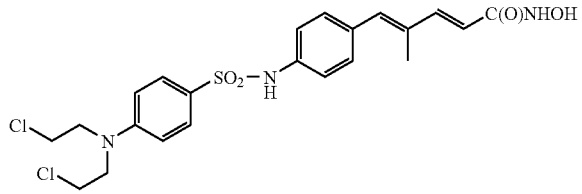

Figure 6:
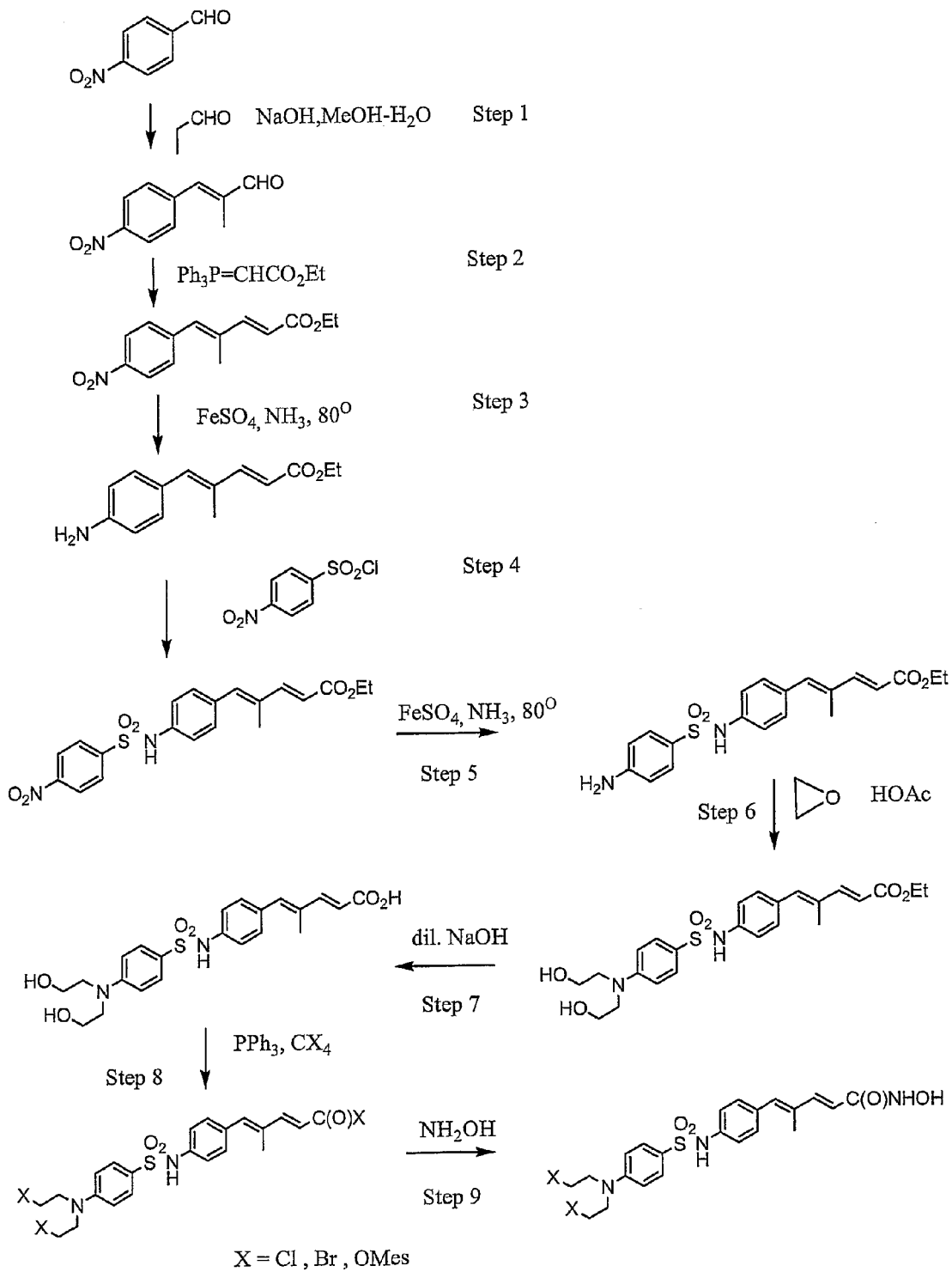
Figure 6A:
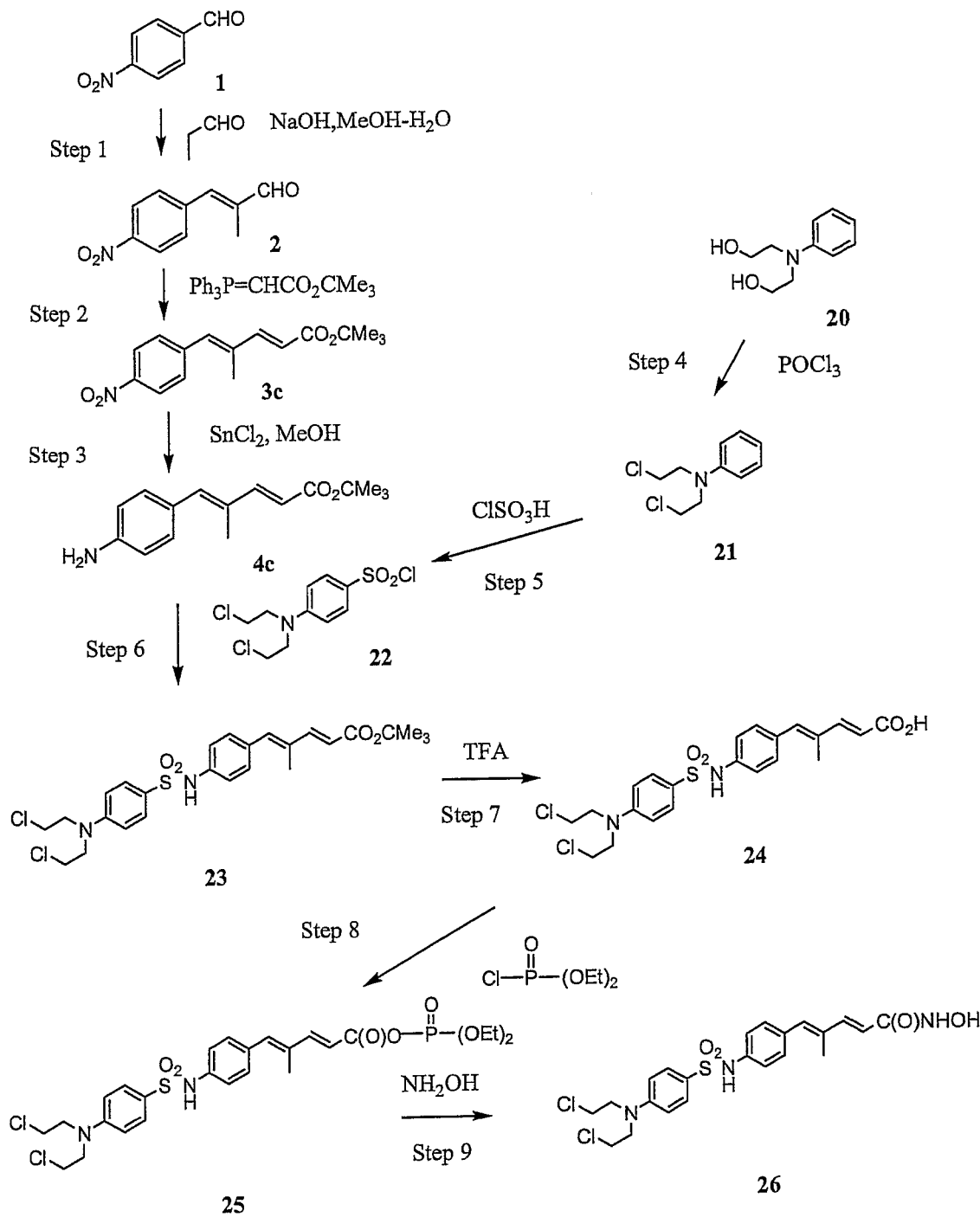
Figure 6B:
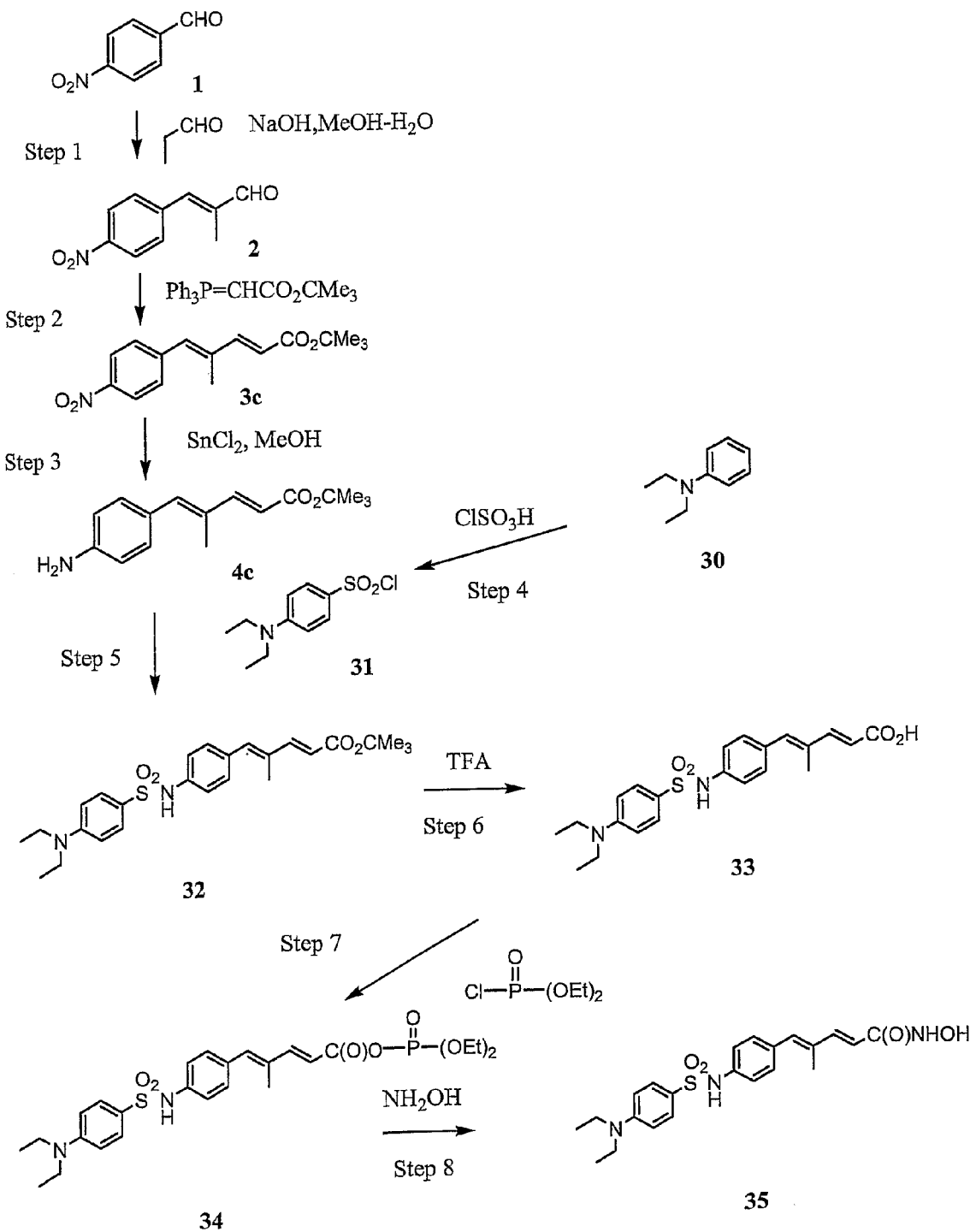
Figure 7:
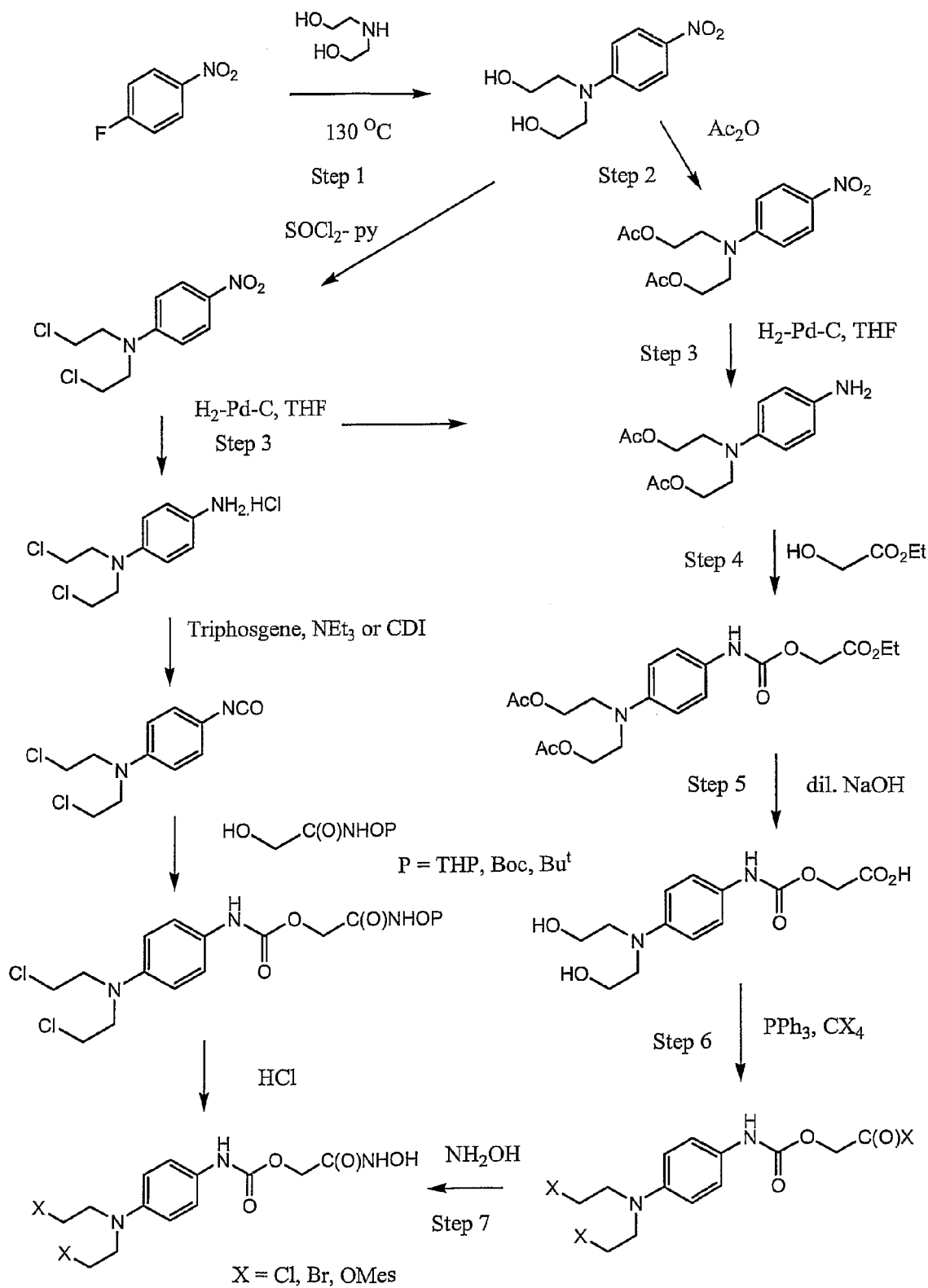
Figure 8:
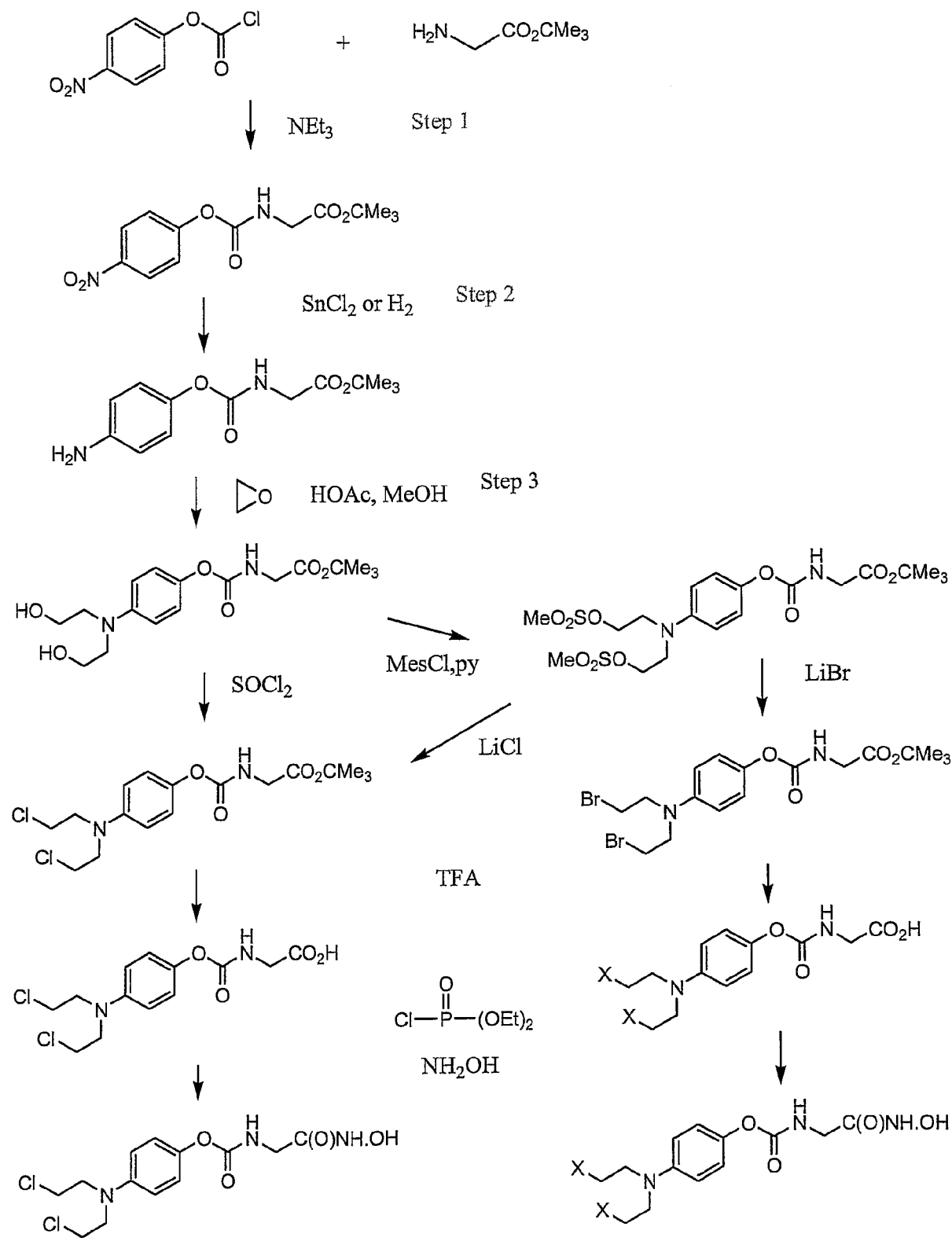

Synthesis was performed as in FIG. 6A.

(E)-2-Methyl-3-(4-nitrophenyl)prop-2-enal (2)

Propionaldehyde (14.3 ml, 11.5 g, 0.20 mol) was added to a solution of 4-nitro benzaldehyde (20.0 g, 0.13 mol) in 50% aqueous ethanol (300 ml). An aqueous solution of 1M sodium hydroxide (36 ml, 0.04 mol) was then added dropwise, with stirring, at room temperature. After stirring for 1.5 h the precipitated solid was collected by filtration and recrystallised from aqueous ethanol to give 19.4 g (77%) of the product as a yellow solid, mp 112-114° C.

$\delta_H$ (500 MHz, CDCl$_3$) 2.09 (3H, s, CH$_3$), 7.33 (1H, brs, H-3), 7.67 (2H, d, J=7 Hz, aromatic H), 8.31 (2H, d, J=7 Hz, aromatic H), 9.66 (1H, s, CHO).

tert-Butyl (E,E)-4-methyl-5-(4-nitrophenyl)penta-2,4-dienoate (3c)

(E)-2-Methyl-3-(4-nitrophenyl)prop-2-enal (3.0 g, 15.6 mmol), (tert-butoxycarbonyl methylene)triphenylphosphorane (8.85 g, 23.4 mmol) and dry acetonitrile (60 ml) were stirred and heated at 65° C. until reaction was complete (ca. 1 h, HPLC monitoring). The mixture was cooled, filtered to remove some insoluble by-product, and the filtrate concentrated in vacuo to ca. 15 ml volume. On cooling the product deposited, was collected by filtration and washed with cold acetonitrile to give a yellow solid (2.4 g), mp 120-122° C. The mother liquors were evaporated to dryness, the residue stirred in ether (20 ml) and the insoluble material removed by filtration. The filtrate was concentrated in vacuo and the residue crystallised from acetonitrile (5 ml) to give a second crop of product (1.3 g). Total yield=3.7 g (87%)

$\delta_H$ (500 MHz, CDCl$_3$) 1.53 (9H, s, CCH$_3$), 2.06 (3H, s, CH$_3$), 6.01 (1H, d, J=15 Hz, H-2), 6.83 (1H, brs, H-5), 7.39 (1H, d, J=15 Hz, H-3), 7.47 (2H, d, J=8 Hz, aromatic H), 8.23 (2H, d, J=8 Hz, aromatic H). m/z 290 (M$^+$+1)

tert-Butyl (E,E)-4-methyl-5-(4-aminophenyl)penta-2,4-dienoate (4c)

Tin(II) chloride dihydrate (11.5 g, 51 mmol) was added to a stirred solution of tert-butyl (E,E)-4-methyl-5-(4-nitrophenyl)penta-2,4-dienoate (3.67 g, 12.7 mmol) in methanol (75 ml). The mixture was stirred and heated at reflux and the reaction monitored by HPLC. After 70 min, 4% starting material remained and there were two new products comprising 90 and 6% respectively. The cool mixture was concentrated in vacuo, water (75 ml) was added to the residue and then 2N NaOH solution until at pH 11. Ethyl acetate (150 ml) was added and the mixture filtered through Celite. The EtOAc layer was washed with 5% NaCl solution, dried over MgSO$_4$ and concentrated in vacuo. The residual oil was stirred in diisopropyl ether (20 ml) for 10 min, insoluble by-products removed by filtration and the filtrate concentrated in vacuo to give 2.8 g (86%) of a yellow solid, mp 99-101° C.

$\delta_H$ (500 MHz, CDCl$_3$) 1.50 (9H, s, CCH$_3$), 2.05 (3H, brs, CH$_3$), 5.90 (1H, d, J=15 Hz, H-2), 6.68 (2H, d, J=8 Hz, aromatic H), 6.74 (1H, brs, H-5), 7.22 (1H, d, J=8 Hz, aromatic H), 7.49 (1H, d, J=15 Hz, H-3).

m/z 260 (M$^+$+1)

N,N-Bis-(2-chloroethylamino)aniline (21) was prepared by the chlorination of phenyl diethanolamine (Aldrich) according to the procedure of Elderfield et al.:

R. C. Elderfield, I. S. Covey, J. B. Geiduschek, W. L. Meyer, A. B. Ross and J. H. Ross, *J. Org. Chem.*, 23, 1749-1753 (1958).

4-(N,N-Bis-2-chloroethylamino)benzenesulfonyl chloride (22)

N,N-Bis-(2-chloroethylamino)aniline (9.1 g, 0.042 mol) was heated to 50-60° C. until molten. Chlorosulfonic acid (10.4 ml, 18.2 g, 0.16 mol) was then added dropwise to the melt (caution! very exothermic) with stirring and cooling in an ice-bath. When the addition was complete the mixture was stirred and heated on a steam bath at 95° C. for 45 min. The cool mixture was poured onto ice-water (200 ml), extracted with dichloromethane (200 ml) and washed with water (70 ml). The dried (MgSO$_4$) extract was concentrated in vacuo, the residual oil triturated in hexane and the solid collected by filtration. Crystallisation of this crude product from ethyl acetate-hexane gave 5.8 g of pale yellow crystals, mp 100-102° C. lit. 102° C. (HPLC purity 99.7%)

Lit.: M. H. Benn, A. M. Creighton, B. J. Johnson, L. N. Owen and G. R. White, *J. Chem. Soc.*, 3395-3400 (1964)

tert-Butyl (E,E)-4-methyl-5-{4-[4-bis-(2-chloroethylamino)phenyl]sulfonamido}-penta-2,4-dienoate (23)

4-(N,N-Bis-2-chloroethylamino)benzenesulfonyl chloride (3.36 g, 11.1 mmol) was added to tert-butyl (E,E)-4-methyl-5-(4-aminophenyl)penta-2,4-dienoate (2.75 g, 10.6 mmol), dry dichloromethane (40 ml) and NaHCO$_3$ (1.78 g, 21.2 mmol). The mixture was stirred and heated at reflux for 18 h, cooled and concentrated in vacuo. The residue was stirred in ether (80 ml) for 0.5 h, filtered to remove inorganic salts, and the filtrate concentrated in vacuo to give a tan gum. This material was chromatographed on silica (150 g). Elution with dichloromethane gave some unreacted starting materials and then the product (3.4 g, 60%) as a pale yellow solid, mp 75-78° C.

$\delta_H$ (500 MHz, CDCl$_3$) 1.51 (9H, s, C(CH$_3$)$_3$), 1.99 (3H, brs, C=CCH$_3$), 3.62 (4H, t, J=7 Hz, 2×NCH$_2$), 3.77 (4H, t, J=7 Hz, 2×CH$_2$Cl), 5.89 (1H, d, J=15.5 Hz, H-2), 6.63 (2H, d, J=8 Hz, aromatic H), 6.70 (1H, brs, NH), 6.79 (1H, brs, H-5), 7.09 (2H, d, J=8 Hz, aromatic H), 7.23 (2H, d, J=8 Hz, aromatic H), 7.35 ((1H, brd, J=15.5 Hz, H-3), 7.68 (2H, d, J=8 Hz, aromatic H). m/z 540 (M$^+$+1)

(E,E)-4-methyl-5-{4-[4-bis-(2-chloroethylamino)phenyl]sulfonamido}penta-2,4-dienoic acid (24)

tert-Butyl (E,E)-4-methyl-5-{4-[4-bis-(2-chloroethylamino)phenyl]sulfonamido}-penta-2,4-dienoate (1.69 g, 3.1 mmol) was dissolved in dry dichloromethane (15 ml) and trifluoroacetic acid (15 ml, 22.2 g, 0.19 mol) added. The solution was stirred and the reaction monitored by HPLC. After 0.5 h no starting ester remained. The volatiles were removed in vacuo, the residue dissolved in dichloromethane and the solution evaporated to dryness (3×) to give the trifluoroacetate (TFA) salt of the product as a yellow solid (1.8 g). m/z 598 (M$^+$+1)

(E,E)-4-Methyl-5-{4-[4-bis-(2-chloroethylamino) phenyl]sulfonamido}penta-2,4-dienoic Acid N-hydroxyamide (26) via (25)

The above salt, (E,E)-4-methyl-5-{4-[4-bis-(2-chloroethylamino)phenyl]sulfonamido}penta-2,4-dienoic acid trifluoroacetate (1.8 g, 3.1 mmol) was dissolved in dry THF (15 ml) and the solution cooled to 5-10° C. Triethylamine (1.27 ml, 0.93 g, 9.2 mmol) was then added followed by diethyl chlorophosphate (0.93 ml, 1.11 g, 6.4 mmol). The mixture was stirred at 5-10° C. for 5 min, allowed to warm to room temperature and monitored by HPLC. After 1.5 h little starting acid remained. A solution of hydroxylamine (0.38 ml of 50% w/v, 6.2 mmol) in water was added and the mixture stirred vigorously. HPLC indicated the reaction was 92% complete after 5 min. The mixture was stirred for 15 min, water (15 ml) added and then a few drops of 2N HCl were added until the mixture was at pH 3. The oily mixture was extracted with dichloromethane (DCM), the DCM layer washed with water and dried over MgSO$_4$. The solvent was removed in vacuo to give a dark yellow gum. This material was crystallised from DCM (40 ml) to give 0.58 g (38%) of product as a yellow solid, mp 140-141° C. HPLC purity 98.5% (C18 column, CH$_3$CN-0.2% TFA in H$_2$O, 45:55, 1 ml/min)

$\delta_H$ (500 MHz, CDCl$_3$) 1.94 (3H, brs, CH$_3$), 3.68-3.80 (8H, m, J=7 Hz, 2×NCH$_2$CH$_2$), 5.92 (1H, d, J=15.5 Hz, H-2), 6.75 (1H, brs, H-5), 6.84 (2H, d, J=9 Hz, aromatic H), 7.12 (2H, d, J=8 Hz, aromatic H), 7.22 ((1H, brd, J=15.5 Hz, H-3), 7.26 (2H, d, J=8 Hz, aromatic H), 7.59 (2H, d, J=9 Hz, aromatic H), 8.94 (1H, brpeak, NH, exchang.), 10.2 (1H, brpeak, OH, exchang.), 10.6 (1H, brpeak, OH, exchang.). m/z 540 (M$^+$+1)

EXAMPLE 4 (COMPARATIVE)

Synthesis of (E,E)-4-methyl-5-{4-[4-(diethylamino) phenyl]sulfonamido}penta-2,4-dienoic acid N-hydroxyamide [C1-B]

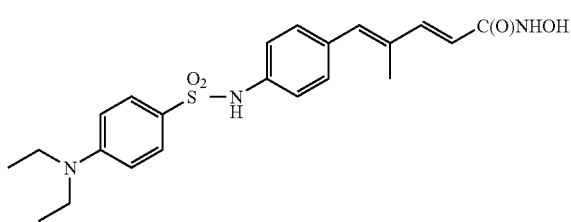

The route is a modification of that for the corresponding nitrogen mustard sulfonamide hydroxamate of Example 3. Synthesis was performed as in FIG. 6B.

(E)-2-Methyl-3-(4-nitrophenyl)prop-2-enal (p-nitro-α-methylcinnamaldehyde) (2)

Propionaldehyde (14.3 ml, 11.5 g, 0.20 mol) was added to a solution of 4-nitro benzaldehyde (20.0 g, 0.13 mol) in 50% aqueous ethanol (300 ml). An aqueous solution of 1M sodium hydroxide (36 ml, 0.04 mol) was then added dropwise, with stirring, at room temperature. After stirring for 1.5 h the precipitated solid was collected by filtration and recrystallised from aqueous ethanol to give 19.4 g (77%) of the product as a yellow solid, mp 112-114° C.

$\delta_H$ (500 MHz, CDCl$_3$) 2.09 (3H, s, CH$_3$), 7.33 (1H, brs, H-3), 7.67 (2H, d, J=7 Hz, aromatic H), 8.31 (2H, d, J=7 Hz, aromatic H), 9.66 (1H, s, CHO).

tert-Butyl (E,E)-4-methyl-5-(4-nitrophenyl)penta-2, 4-dienoate (3c)

(E)-2-Methyl-3-(4-nitrophenyl)prop-2-enal (3.0 g, 15.6 mmol), (tert-butoxycarbonyl methylene)triphenylphosphorane (8.85 g, 23.4 mmol) and dry acetonitrile (60 ml) were stirred and heated at 65° C. until reaction was complete (ca. 1 h, HPLC monitoring). The mixture was cooled, filtered to remove some insoluble by-product, and the filtrate concentrated in vacuo to ca. 15 ml volume. On cooling the product deposited, was collected by filtration and washed with cold acetonitrile to give a yellow solid (2.4 g), mp 120-122° C. The mother liquors were evaporated to dryness, the residue stirred in ether (20 ml) and the insoluble material removed by filtration. The filtrate was concentrated in vacuo and the residue crystallised from acetonitrile (5 ml) to give a second crop of product (1.3 g). Total yield=3.7 g (87%)

$\delta_H$ (500 MHz, CDCl$_3$) 1.53 (9H, s, CCH$_3$), 2.06 (3H, s, CH$_3$), 6.01 (1H, d, J=15 Hz, H-2), 6.83 (1H, brs, H-5), 7.39 (1H, d, J=15 Hz, H-3), 7.47 (2H, d, J=8 Hz, aromatic H), 8.23 (2H, d, J=8 Hz, aromatic H). m/z 290 (M$^+$+1)

tert-Butyl (E,E)-4-methyl-5-(4-aminophenyl)penta-2, 4-dienoate (4c)

Tin(ii) chloride dihydrate (11.5 g, 51 mmol) was added to a stirred solution of tert-butyl (E,E)-4-methyl-5-(4-nitrophenyl)penta-2,4-dienoate (3.67 g, 12.7 mmol) in methanol (75 ml). The mixture was stirred and heated at reflux and the reaction monitored by HPLC. After 70 min, 4% starting material remained and there were two new products comprising 90 and 6% respectively. The cool mixture was concentrated in vacuo, water (75 ml) was added to the residue and then 2N NaOH solution until at pH 11. Ethyl acetate (150 ml) was added and the mixture filtered through Celite. The EtOAc layer was washed with 5% NaCl solution, dried over MgSO$_4$ and concentrated in vacuo. The residual oil was stirred in diisopropyl ether (20 ml) for 10 min, insoluble by-products removed by filtration and the filtrate concentrated in vacuo to give 2.8 g (86%) of a yellow solid, mp 99-101° C.

$\delta_H$ (500 MHz, CDCl$_3$) 1.50 (9H, s, CCH$_3$), 2.05 (3H, brs, CH$_3$), 5.90 (1H, d, J=15 Hz, H-2), 6.68 (2H, d, J=8 Hz, aromatic H), 6.74 (1H, brs, H-5), 7.22 (1H, d, J=8 Hz, aromatic H), 7.49 (1H, d, J=15 Hz, H-3).

m/z 260 (M$^+$+1)

N/N-Diethylaniline (30) is available commercially.

4-(N,N-Diethylamino)benzenesulfonyl chloride (31) was prepared via reaction of N,N-diethylaniline with trimethylsilyl chlorosulfonate. The resulting 4-diethylamino-benzenesulfonic acid was reacted with phosphorus pentachloride according to the procedure of E. Toja et al, Arzneim.-Forsch., 44, 501-509 (1994) to give the sulfonyl chloride as a yellow solid, mp 79-81° C. lit. mp 79-81° C.

tert-Butyl (E,E)-4-methyl-5-{4-[4-diethylamino) phenyl]sulfonamido}penta-2,4-dienoate (32)

4-(N,N-diethylamino)benzenesulfonyl chloride (2.34 g, 9.5 mmol) was added to tert-butyl (E,E)-4-methyl-5-(4-aminophenyl)penta-2,4-dienoate (2.45 g, 9.5 mmol), dry dichloromethane (25 ml) and NaHCO$_3$ (1.59 g, 19 mmol). The mixture was stirred and heated at reflux for 18 h, cooled and concentrated in vacuo. The residue was stirred in ether (60 ml) for 0.5 h, filtered to remove inorganic salts, and the filtrate concentrated in vacuo to give a tan gum. This material was chromatographed on silica (100 g). Elution with dichloromethane gave, after removal of some unreacted starting materials, and trituration in ether the product (2.68 g, 60%) as a white solid, mp 198-200° C.

$\delta_H$(500 MHz, CDCl$_3$) 1.06 (6H, t, J=7 Hz, 2×CH3), 1.51 (9H, s, C(CH$_3$)$_3$), 1.97 (3H, brs, C=CCH$_3$), 3.35 (4H, t, J=7 Hz, 2×NCH$_2$), 5.89 (1H, d, J=15.5 Hz, H-2), 6.63 (2H, d, J=8 Hz, aromatic H), 6.70 (1H, brs, NH), 6.79 (1H, brs, H-5), 7.09 (2H, d, J=8 Hz, aromatic H), 7.23 (2H, d, J=8 Hz, aromatic H), 7.35 ((1 H, brd, J=15.5 Hz, H-3), 7.68 (2H, d, J=8 Hz, aromatic H). m/z 471 (M$^+$+1)

(E,E)-4-methyl-5-{4-[4-(diethylamino)phenyl] sulfonamido}penta-2,4-dienoic acid (33)

tert-Butyl (E,E)-4-methyl-5-{4-[4-(diethylamino)phenyl] sulfonamido}penta-2,4-dienoate (0.50 g, 1.1 mmol) was dissolved in dry dichloromethane (5 ml) and trifluoroacetic acid (5 ml, 7.4 g, 63 mmol) added. The solution was stirred and the reaction monitored by HPLC. After 0.5 h no starting ester remained. The volatiles were removed in vacuo, the residue dissolved in dichloromethane and the solution evaporated to dryness (3×) to give the trifluoroacetate (TFA) salt of the product as a yellow gum (0.5 g). m/z 415 (M$^+$+1)

(E,E)-4-methyl-5-{4-[4-(diethylamino)phenyl] sulfonamido}penta-2,4-dienoic acid N-hydroxyamide (35) via (34)

The above salt, (E,E)-4-methyl-5-{4-[4-(diethylamino) phenyl] sulfonamido}penta-2,4-dienoic acid trifluoroacetate (0.50 g, 1.1 mmol) was dissolved in dry THF (5 ml) and the solution cooled to 5-10° C. Triethylamine (0.44 ml, 0.32 g, 3.2 mmol) was then added followed by diethyl chlorophosphate (0.31 ml, 0.37 g, 2.1 mmol). The mixture was stirred at 5-10° C. for 5 min, allowed to warm to room temperature and monitored by HPLC. After 2.5 h little starting acid remained. A solution of hydroxylamine (0.26 ml of 50% w/v, 4.2 mmol) in water was added and the mixture stirred vigorously. HPLC indicated the reaction was 90% complete after 5 min. The mixture was stirred for 15 min, water (5 ml) added and then a few drops of 2N HCl were added until the mixture was at pH 3. The oily mixture was extracted with dichloromethane (DCM), the DCM layer washed with water and dried over MgSO$_4$. The solvent was removed in vacuo to give a dark yellow gum. This material was crystallised from DCM (10 ml) to give 0.14 g (30%) of product as a yellow solid, mp 142-144° C. (decomp.). HPLC purity 95.8% (C18 column, CH$_3$CN-0.2% TFA in H$_2$O, 35:65, 1 ml/min) $\delta_H$(500 MHz, dmso-d6) 1.06 (3H, t, J=7 Hz, 2×CH$_3$), 1.92 (3H, brs, =CCH$_3$), 3.40 (4H, m, q at 50° C., J=7 Hz, 2×NCH$_2$), 5.92 (1H, d, J=15.5 Hz, H-2), 6.67 (2H, d, J=8 Hz, aromatic H), 6.75 (1H, brs, H-5), 7.11 (2H, d, J=8 Hz, aromatic H), 7.22 ((1H, brd, J=15.5 Hz, H-3), 7.26 (2H, d, J=8 Hz, aromatic H), 7.53 (2H, d, J=8 Hz, aromatic H), 8.94 (1H, brs, NH, exchang.), 10.1 (1H, brs, OH, exchang.), 10.6 (1H, brs, OH, exchang.). m/z 430 (M$^+$+1)

EXAMPLE 5

HDAC Assay Using the Fluor de Lys Assay Kit

FIG. 9 shows in vitro HDAC assay data performed using HeLa nuclear extract and the Fluor-de-Lys assay kit (BIOMOL) on the dichloro compound of Example 3 [C1-A] and the comparative compound of Example 4 [C1-B]. Trichostatin A (TSA) was used as control. Depudecin was also used as control and gave an EC$_{50}$ value of >10 μM. Results from two sets of independent assays are shown in Table 1.

TABLE 1

| Drug | Average EC$_{50}$ (M) | SE | Average EC$_{50}$ (M) | SE | N (for each replicate) |
|---|---|---|---|---|---|
| C1-A | 5.9E-07 | 2.1E-08 | 3.1E-07 | 2.0E-08 | 3 |
| C1-B | 3.2E-07 | 9.4E-08 | 4.5E-07 | 5.8E-08 | 3 |
| TSA | 3.5E-09 | 8.9E-10 | 3.5E-09 | 1.5E-10 | 3 |

EXAMPLE 6

SRB Assay

FIG. 10 shows in vitro SRB assay data in MCF-7 cells on the dichloro compound of Example 3 [C1-A] and the comparative compound of Example 4 [C1-B]. Trichostatin A (TSA) was used as control. Data from two independent assays are summarised in Table 2.

TABLE 2

| Drug | Average EC$_{50}$ (M) | SE | Average EC$_{50}$ (M) | SE | N (for each replicate) |
|---|---|---|---|---|---|
| C1-A | 3.9E-06 | 6.5E-07 | 6.8E-06 | 5.2E-07 | 5-6 |
| C1-B | 6.0E-06 | 4.8E-07 | 1.4E-05 | 3.5E-06 | 5-6 |
| TSA | 7.5E-08 | 8.4E-09 | 1.1E-07 | 3.3E-10 | 5-6 |

EXAMPLE 7

Reversible HDAC1 Assay Using the Fluor-de-Lys Assay Kit

Figure 11:
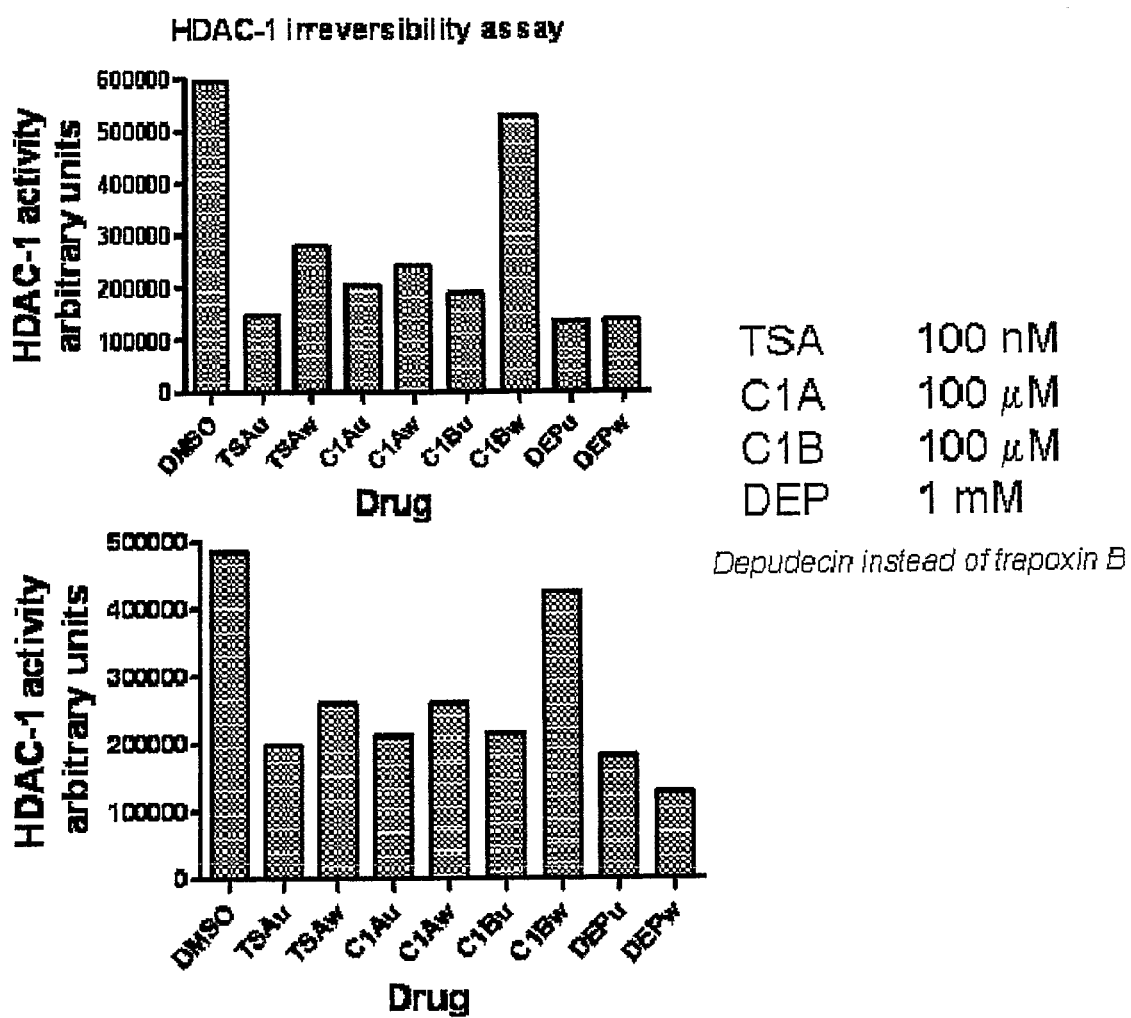

FIG. 11 shows in vitro HDAC1 inhibition data with or without washing to demonstrate irreversibility of the dichloro compound of Example 3 [C1-A] and the comparative compound of Example 4 [C1-B]. Depudecin was used as control.

EXAMPLE 8

Reversible SRB Assay

Figure 12:
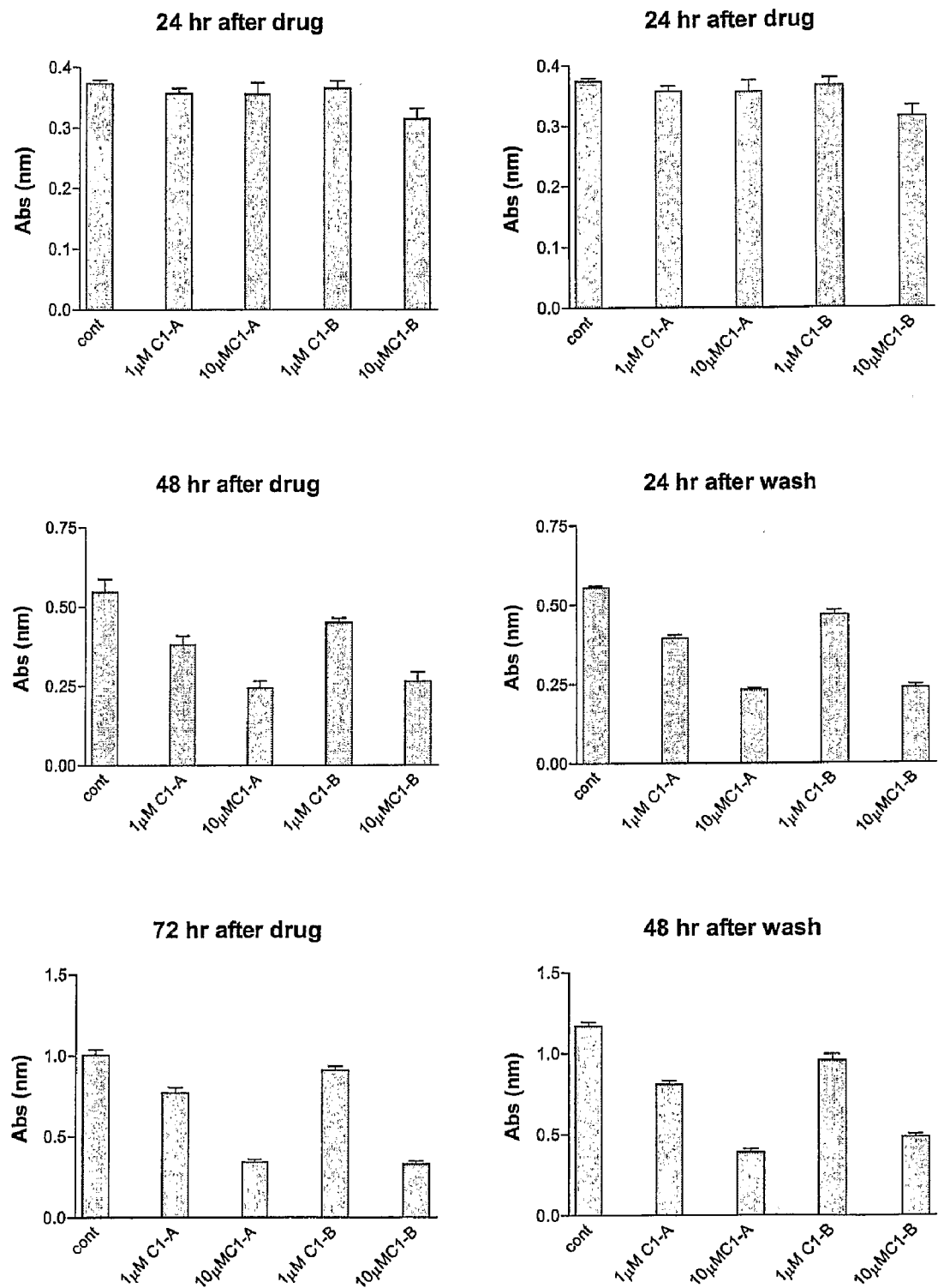

FIG. 12 shows in vitro SRB inhibition data in MCF-7 cells with or without washing to demonstrate irreversibility of the dichloro compound of Example 3 [C1-A] and the comparative compound of Example 4 [C1-B].

EXAMPLE 9

Inhibition of pRb & Cyclin D and the Induction of H4 Hyperacetylation by CIA

FIG. 13 shows western blots of the dichloro compound of Example 3 [C1-A] and the comparative compound of Example 4 [C1-B] on Histone H4 acetylation (left panel) and their effect on retinoblastoma protein (pRb) and Cyclin D1 (right panel) in MCF-7 cells. MCF-7 cells were treated with drug or vehicle (equivalent concentration of DMSO in growth media) for 24 h. Cells were harvested and homogenised. The respective proteins (acetyl-H4, pRb and cyclin D1) in supernatants of these homogenates were visualised by western blot analysis as previously described (Leyton J. et al., Cancer Res. (2006) 66(15): 7621-9).

EXAMPLE 10

Pharmacokinetic Studies In Vivo after Intravenous Injection

FIG. 14 shows the results of intravenous (i.v.) pharmacokinetic studies in vivo with the dichloro compound of Example 3 [C1-A]. C1-A at 80 mg/kg in 10% DMSO, 5% Tween 20 and 85% saline was injected i.v. into the mouse. Plasma samples were deproteinated with two volume equivalents of methanol, then 200 µl was analysed by reversed-phase high pressure liquid chromatography (5 µm C18 column and 10 mM ammonium acetate/acetonitrile gradient) with ultraviolet detection at a wavelength of 351 nm. C1-A was detectable in plasma up to 60 min after i.v. injection. This can be compared with experiments with TSA, which demonstrated almost no parent drug and 17 UV metabolites at 20 minutes (Sanderson et al, 2004). FIG. 14 also shows that C1-A was detectable in the liver at all time points and with a similar metabolic profile as in the plasma.

EXAMPLE 11

Efficacy of C1-A In Vivo

Figure 15:
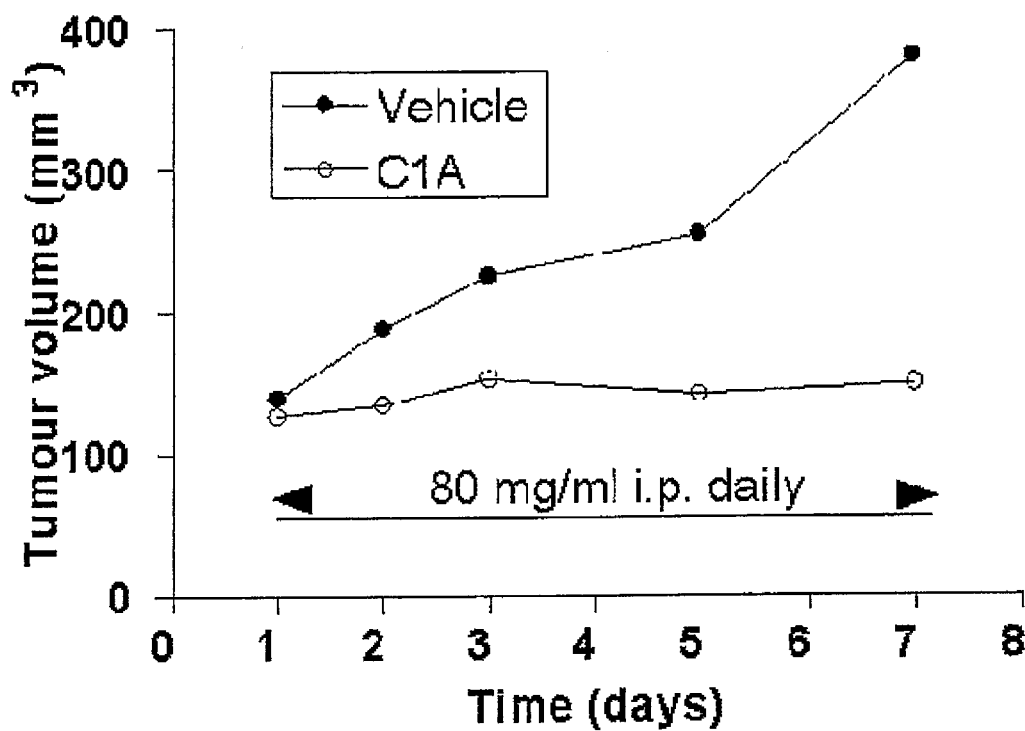

FIG. 15 shows the results of a study on the efficacy of C1-A in vivo. The study was carried out at n=1 each for drug- or vehicle-treated mice. HCT116 human colon cancer cells were injected subcutaneously into the back of mice to form tumours.

When the tumours were about ~125 mm$^3$, the mice were injected with C1-A at 80 mg/ml or vehicle (10% DMSO, 5% Tween 20 and 85% saline) intraperitoneally daily for 7 days. Tumour sizes were measured every 1-2 days in 3 orthogonal axes by callipers to determine tumour volume. Tumour volume was greater in the control than in the C1-A-treated mouse. Based on measurement of body weight, no toxicity was detectable in the mice.

EXAMPLE 12

Intraperitoneal Pharmacokinetic Studies In Vivo

Figure 16:
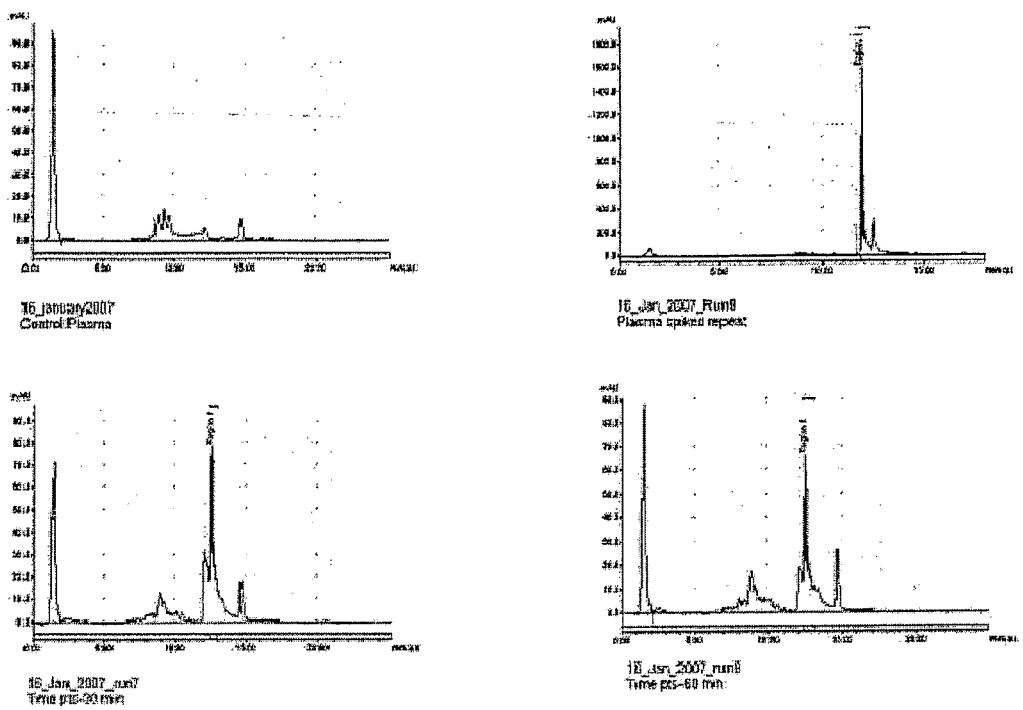
Figure 17:
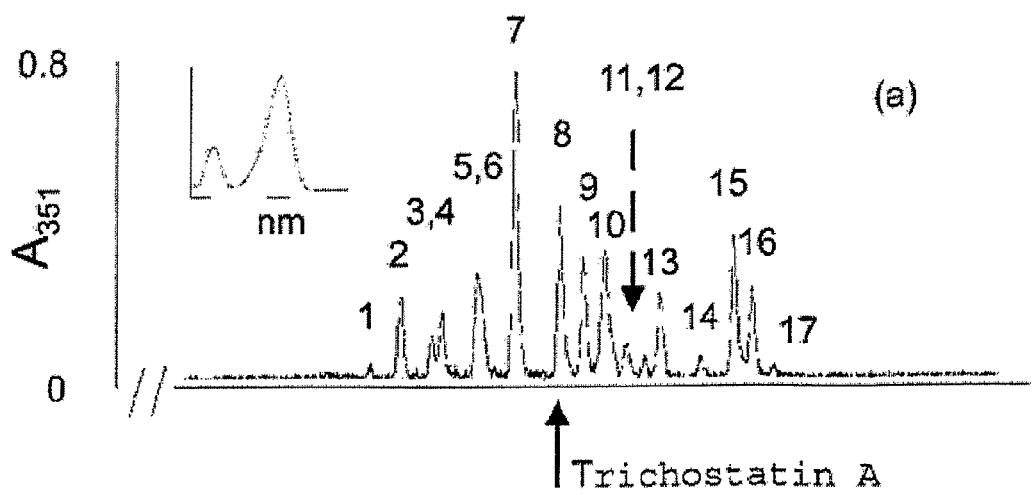

FIG. 16 shows the results of early intraperitoneal (i.p.) pharmacokinetic studies in vivo with the dichloro compound of Example 3 [C1-A]. C1-A was introduced at 80 mg/kg in DMSO (0.0015 ml/g; 30 µl) intraperitoneally into the mouse. The HPLC-UV plots show that C1-A was stable in vivo in the mouse. FIG. 16 shows that with C1-A only 5 UV metabolites were seen at 60 minutes. This can be compared with similar experiments with TSA (after i.p. introduction at 80 mg/kg into mice), which demonstrated 17 UV metabolites at 20 minutes (FIG. 17 and Sanderson et al, 2004).

The invention claimed is:
1. A compound of formula I,

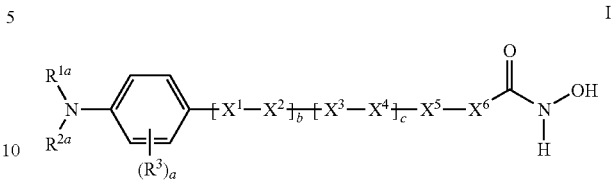

wherein
R$^{1a}$ represents C$_{1-4}$ alkyl (which latter group is optionally substituted by one or more substituents selected from halogeno and aryl), aryl, (CH$_2$)$_2$-L$^1$ or the structural fragment

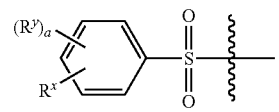

wherein R$^x$ represents H or N(R$^{1b}$)R$^{2b}$;
R$^{1b}$ and R$^{2b}$ independently represent C$_{1-4}$ alkyl (which latter group is optionally substituted by one or more substituents selected from halogeno and aryl), aryl or (CH$_2$)$_2$-L$^2$;
R$^y$ represents halogeno or C$_{1-4}$ alkyl;
R$^{2a}$ represents H, C$_{1-4}$ alkyl (which latter group is optionally substituted by one or more substituents selected from halogeno and aryl), aryl or (CH$_2$)$_2$-L$^3$;
L$^1$, L$^2$ and L$^3$ each represents, independently at each occurrence, a leaving group;
R$^3$ represents halogeno or C$_{1-4}$ alkyl;
a represents, independently at each occurrence, an integer from 0 to 4;
X$^1$—X$^2$ represents C(O)—CH(Y$^1$), C(H)═C(Y$^1$), CH$_2$—CH(Y$^1$), NH—CH(Y$^1$), CH$_2$—C(O), NH—C(O) or CH(Y$^1$);
b represents 0 or 1;
X$^3$—X$^4$ represents CH═C(Y$^2$), O—CH(Y$^2$), NH—CH(Y$^2$), O—C(O) or NH—C(O);
c represents an integer from 0 to 10;
X$^5$—X$^6$ represents CH$_2$—CH$_2$, CH═CH or O—CH$_2$; and
Y$^1$ and Y$^2$ independently represent, at each occurrence, H or C$_{1-4}$ alkyl;
or a pharmaceutically acceptable derivative thereof,
provided that at least one of the following is the case:
(a) R$^{1a}$ represents (CH$_2$)$_2$-L$^1$;
(b) R$^{1b}$ and/or R$^{2b}$ represents (CH$_2$)$_2$-L$^2$;
(c) R$^2$ represents (CH$_2$)$_2$-L$^3$.
2. A compound of formula I,

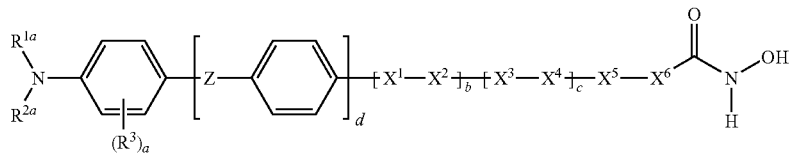

wherein
R$^{1a}$ represents C$_{1-4}$ alkyl (which latter group is optionally substituted by one or more substituents selected from halogeno and aryl), aryl or (CH$_2$)$_2$-L$^1$;
R$^{2a}$ represents H, C$_{1-4}$ alkyl (which latter group is optionally substituted by one or more substituents selected from halogeno and aryl), aryl or (CH$_2$)$_2$-L$^3$;
L$^1$, L$^2$ and L$^3$ each represents, independently at each occurrence, a leaving group;
R$^3$ represents halogeno or C$_{1-4}$ alkyl;
a represents, independently at each occurrence, an integer from 0 to 4;
X$^1$—X$^2$ represents C(O)—CH(Y$^1$), C(H)=C(Y$^1$), CH$_2$—CH(Y$^1$), NH—CH(Y$^1$), CH$_2$—C(O), NH—C(O) or CH(Y$^1$);
b represents 0 or 1;
X$^3$—X$^4$ represents CH=C(Y$^2$), O—CH(Y$^2$), NH—CH(Y$^2$), O—C(O) or NH—C(O);
c represents an integer from 0 to 10;
Z represents —SO$_2$.NH— or —NH.SO$_2$—;
d represents 0 or 1;
X$^5$—X$^6$ represents CH$_2$—CH$_2$, CH=CH or O—CH$_2$; and
Y$^1$ and Y$^2$ independently represent, at each occurrence, H or C$_{1-4}$ alkyl;
or a pharmaceutically acceptable derivative thereof,
provided that at least one of the following is the case:
(a) R$^{1a}$ represents (CH$_2$)$_2$-L$^1$;
(c) R$^{2a}$ represents (CH$_2$)$_2$-L$^3$.

3. A compound as claimed in claim 1 wherein L$^1$ or L$^2$ represents, independently at each occurrence, a halogeno group or OS(O)$_2$R$^4$, wherein R$^4$ is C$_{1-8}$ alkyl (optionally substituted by one or more fluoro atoms) or aryl (optionally substituted by one or more substituents selected from C$_{1-4}$ alkyl, C$_{1-4}$ alkoxy, NO$_2$ and halogeno).

4. A compound as claimed in claim 3 wherein L$^1$ or L$^2$ represents, independently at each occurrence, Cl, Br, I or CH$_3$SO$_2$O (mesyloxy).

5. A compound as claimed in claim 1 wherein R$^{1a}$ represents (CH$_2$)$_2$-L$^1$ or the structural fragment

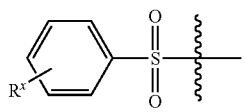

wherein R$^x$ is as defined in claim 1.

6. A compound as claimed in claim 5 wherein R$^x$ represents N(R$^{1b}$)R$^{2b}$ attached in the 4-position relative to the S(O)$_2$ moiety.

7. A compound as claimed in claim 1 wherein R$^{1b}$ and R$^{2b}$ both represent (CH$_2$)$_2$-L$^2$.

8. A compound as claimed in claim 1 wherein R$^2$ represents (CH$_2$)$_2$-L$^3$ or, when R$^x$ represents N(R$^{1b}$)R$^{2b}$, then R$^2$ represents H.

9. A compound as claimed in claim 1 wherein a represents 0.

10. A compound as claimed in claim 1 wherein X$^1$—X$^2$ represents C(O)—CH(Y$^1$), C(H)=C(Y$^1$) or NH—C(O).

11. A compound as claimed in claim 1 wherein b represents 1.

12. A compound as claimed in claim 1 wherein X$^3$—X$^4$ represents CH=C(Y$^2$).

13. A compound as claimed in claim 1 wherein c represents an integer from 0 to 3.

14. A compound as claimed in claim 1 wherein X$^5$—X$^6$ represents CH=CH or O—CH$_2$.

15. A compound as claimed in claim 1 wherein Y$^1$ and Y$^2$ independently represent, at each occurrence, H or C$_{1-2}$ alkyl.

16. A compound as claimed in claim 1 which is a compound of formula Ia, Ib, Ib', Ic, Ic', Id or Ie:

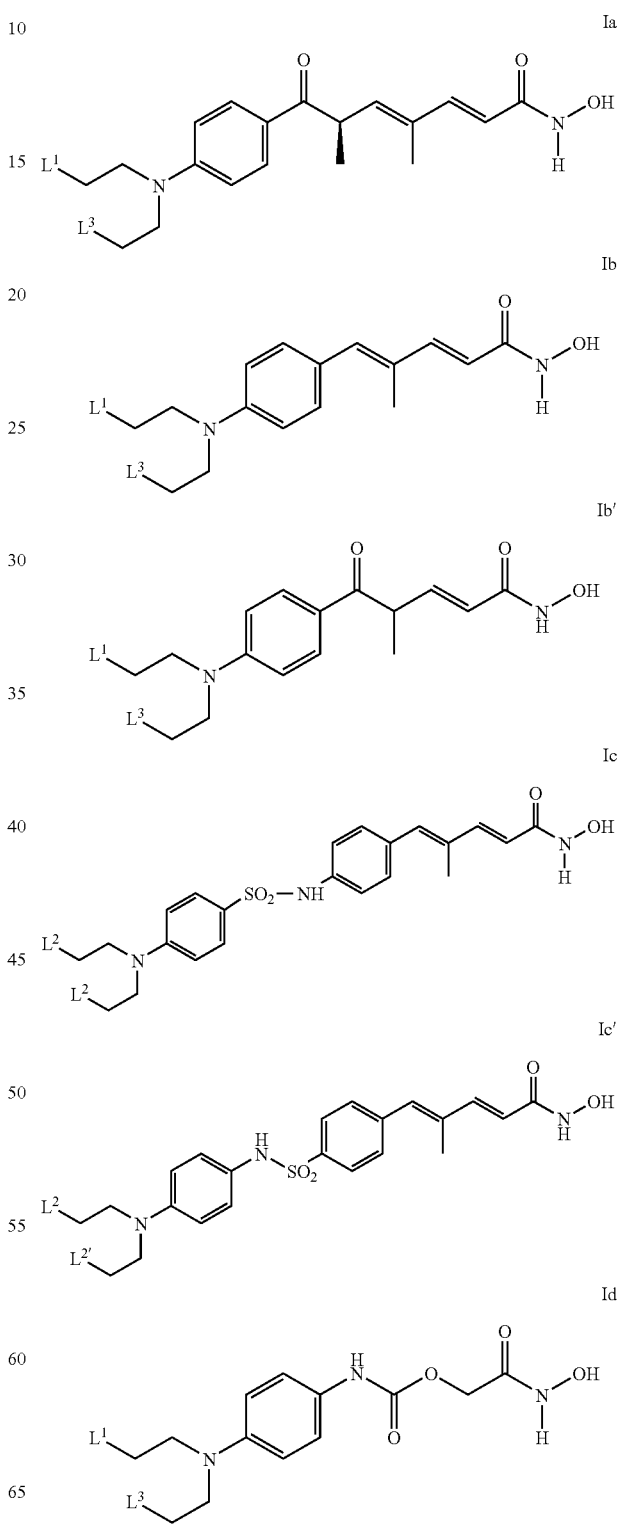

-continued

Ie

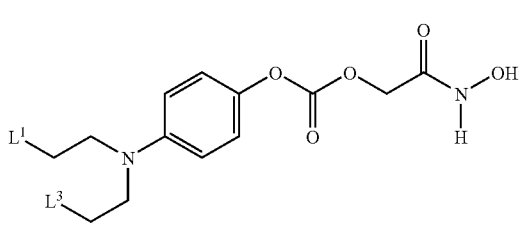

wherein $L^1$, $L^2$ and $L^3$ are as defined in any one of claims 1 to 3 and $L^{2'}$ represents a further leaving group, defined as for $L^2$ in any one of claims 1 to 3.

17. A pharmaceutical composition comprising a compound as defined in claim 1 and a pharmaceutically acceptable carrier.

18. A pharmaceutical composition as claimed in claim 17 further comprising one or more anticancer agents.

19. A process for the preparation of a compound of formula I, as defined in claim 1, which process comprises:

(a) for compounds of formula I in which $L^1$, $L^2$ and/or $L^3$ represents halogeno, halogenation of a corresponding compound of formula II,

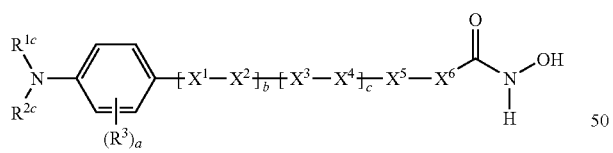

II wherein $R^{1c}$ represents $C_{1-4}$ alkyl (which latter group is optionally substituted by one or more substituents selected from halogeno and aryl), aryl, $(CH_2)_2$—OH or the structural fragment

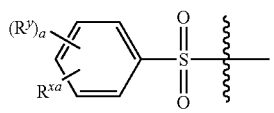

wherein $R^{xa}$ represents H or $N(R^{1d})R^{2d}$, $R^{1d}$ and $R^{2d}$ independently represent $C_{1-4}$ alkyl (which latter group is optionally substituted by one or more substituents selected from halogeno and aryl), aryl or $(CH_2)_2$—OH, $R^{2c}$ represents H, $C_{1-4}$ alkyl (which latter group is optionally substituted by one or more substituents selected from halogeno and aryl), aryl or $(CH_2)_2$—OH, and $R^y$, $R^3$, $X^1$ to $X^6$, a, b and c are as defined in claim 1, provided that at least one of $R^{1c}$, $R^{2c}$, $R^{1d}$ and $R^{2d}$ represents $(CH_2)_2$—OH;

(b) for compounds of formula I in which $L^1$, $L^2$ and/or $L^3$ represents $OS(O)_2R^4$, reaction of a compound of formula II, as defined above, with a compound of formula III, $$R^4S(O)_2\text{-}L^4 \quad\quad\quad\quad III$$

wherein $L^4$ represents a leaving group and $R^4$ is as defined in claim 2;

(c) for compounds of formula I in which either $L^1$ and $L^3$ both represent chloro, or in which $R^{2a}$ is other than $(CH_2)_2\text{-}L^3$ and $N(R^{1b})R^{2b}$ represents $N((CH_2)_2Cl)_2$, reaction of a compound of formula IVA or of formula IVB

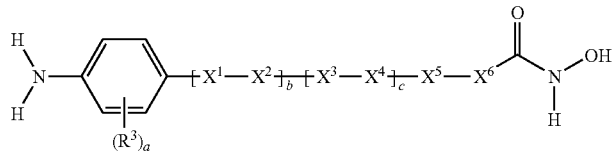

IVA

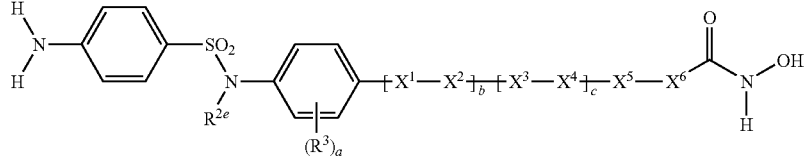

IVB wherein $R^{2e}$ takes the same definition as $R^{2a}$ in claim 1, except that it does not represent $(CH_2)_2\text{-}L^3$, and $R^3$, $X^1$ to $X^6$, a, b and c are as defined, in claim 1, with two or more equivalents of chloroacetaldehyde, either in the presence of, or followed by the addition of, a reducing agent;

(d) reaction of a compound of formula V,

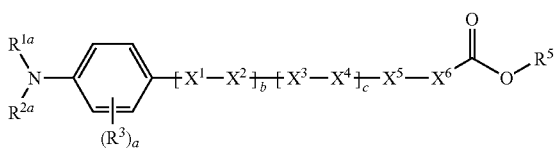

V wherein $R^5$ represents $C_{1-4}$ alkyl and $R^{1a}$, $R^{2a}$, $R^3$, $X^1$ to $X^6$, a, b and c are as hereinbefore defined, with hydroxylamine, or a suitable salt thereof (e.g. hydroxylamine hydrochloride), for example under conditions known to those skilled in the art (e.g. in the presence of a suitable solvent (such as water) and an appropriate base (such as potassium hydroxide)); or (e) reaction of a compound of formula V, wherein $R^5$ represents hydrogen and $R^{1a}$, $R_{2a}$, $R^3$, $X^1$ to $X^6$, a, b and c are as hereinbefore defined, with a coupling agent, followed by reaction with hydroxylamine, or a suitable salt thereof, in the presence of a suitable solvent and an appropriate base.

20. A compound of formula II, as produced in claim 19, or a protected derivative thereof.

21. A compound of formula:

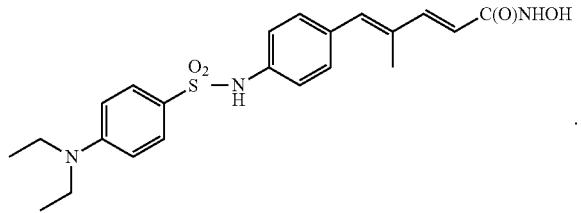

UNITED STATES PATENT AND TRADEMARK OFFICE
CERTIFICATE OF CORRECTION

PATENT NO.         : 8,236,985 B2                               Page 1 of 1
APPLICATION NO.    : 12/447006
DATED              : August 7, 2012
INVENTOR(S)        : Eric O. Aboagye and David M. Vigushin It is certified that error appears in the above-identified patent and that said Letters Patent is hereby corrected as shown below:

In claim 19, at col. 33, line 41, delete "$L^{l}$" and insert --$L^{1}$--.
In claim 19, at col. 35, line 5, delete "$R_{2a}$" and insert --$R^{2a}$--.

Signed and Sealed this
Fifth Day of February, 2013

Teresa Stanek Rea
*Acting Director of the United States Patent and Trademark Office*